US008486393B2

(12) United States Patent
Ferrone et al.

(10) Patent No.: US 8,486,393 B2
(45) Date of Patent: Jul. 16, 2013

(54) MONOCLONAL ANTIBODIES FOR CSPG4 FOR THE DIAGNOSIS AND TREATMENT OF BASAL BREAST CARCINOMA

(75) Inventors: Soldano Ferrone, Pittsburgh, PA (US); Xinhui Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 120 days.

(21) Appl. No.: 13/119,428

(22) PCT Filed: Sep. 18, 2009

(86) PCT No.: PCT/US2009/057578
§ 371 (c)(1),
(2), (4) Date: Mar. 16, 2011

(87) PCT Pub. No.: WO2010/033866
PCT Pub. Date: Mar. 25, 2010

(65) Prior Publication Data
US 2011/0171229 A1    Jul. 14, 2011

Related U.S. Application Data

(60) Provisional application No. 61/098,548, filed on Sep. 19, 2008.

(51) Int. Cl.
*A61K 39/395* (2006.01)

(52) U.S. Cl.
USPC ...................................... 424/130.1

(58) Field of Classification Search
None
See application file for complete search history.

(56) References Cited

U.S. PATENT DOCUMENTS

2004/0197328 A1    10/2004    Young et al.

FOREIGN PATENT DOCUMENTS

| EP | 0 380 607 | 12/1994 |
|---|---|---|
| WO | WO 89/11296 | 11/1989 |
| WO | WO 2006/045750 A2 | 5/2006 |
| WO | WO 2006/100582 A1 | 9/2006 |
| WO | WO 2007/109193 | 9/2007 |

OTHER PUBLICATIONS

Wang et al (AACR, 2007, 48: 1321).*
Hollestelle et al (Breast Cancer Res Treat, 2010, 121: 53-64).*
Ghose et al (Cancer Immunol Immunother, 1991, 34(2): Abstract).*
Orlando et al (BMC Cancer, 2006, 6: Abstract).*
Arteaga et al (Cancer Res, 1994, 54(17): Abstract).*
Dell'Erba et al (Anticancer Research, 2001, 21: 925-930).*
International Search Report from parent PCT Application No. PCTUS2009/057578, 7 pages (mailed Apr. 2, 2010).
Written Opinion from parent PCT Application No. PCTUS2009/057578, 4 pages (mailed Apr. 2, 2010).
Yeo et al., "Alterations in Proteoglycan Synthesis Common to Healing Wounds and Tumors," *Am. J. Pathol.* 138(6):1437-1450 (Jun. 1991).
Mittelman et al., "Human high molecular weight melanoma-associated antigen (HMW-MAA) mimicry by mouse anti-idiotypic monoclonal antibody MK2-23: Induction of humoral anti-HMW-MAA immunity and prolongation of survival on patients with stage IV melanoma," *Proc. Natl. Acad. Sci.* 89:466-470 (Jan. 1, 1992).
Wang et al., "Antibody-based immunotherapy: targeting HMW-MAA on human breast cancer stem cells," *AACR* 48:1321 (Apr. 1, 2007).
Wang et al., "CSPG4 protein as a new target for the antibody-based immunotherapy of triple-negative breast cancer," *JNCI* 102(19):1496-1512 (Oct. 6, 2010).
Li et al., "Intrinsic resistance of tumorigenic breast cancer cells to chemotherapy," *Journal of the National Cancer Institute* 100:672-679 (2008).
Lin et al., "CD44+/CD24− phenotype contributes to malignant relapse following surgical resection and chemotherapy in patients with invasive ductal carcinoma," *Journal of Experimental & Clinical Cancer Research* 31:59 (2012).
Rae et al., "MDA-MB-435 cells are derived from M14 Melanoma cells-a loss for breast cancer, but a boon for melanoma research," *Breast Cancer Research and Treatment* 104(1):13-19 (Jul. 2007).
Wang et al., "Antibody-based immunotherapy: targeting HMW-MAA on human breast cancer stem cells," Poster for 98th AACR Annual Meeting(Apr. 14-19, 2007).

* cited by examiner

*Primary Examiner* — Sean Aeder
(74) *Attorney, Agent, or Firm* — Klarquist Sparkman, LLP

(57) ABSTRACT

It is disclosed herein that condroitin sulfate proteoglycan 4 (CSPG4), also known as high molecular weight melanoma associated antigen, is overexpressed on basal breast carcinoma cells (BBC), specifically triple negative basal breast carcinoma cells (TNBC). Methods for detecting basal breast cancer in a subject are disclosed. Methods are also disclosed for inhibiting the growth of a basal breast cancer cell. These methods include contacting the basal breast cancer cell with an effective amount of an antibody that specifically binds CSPG4. Additional treatment methods, and the use of antibody panels, are also described herein.

12 Claims, 14 Drawing Sheets

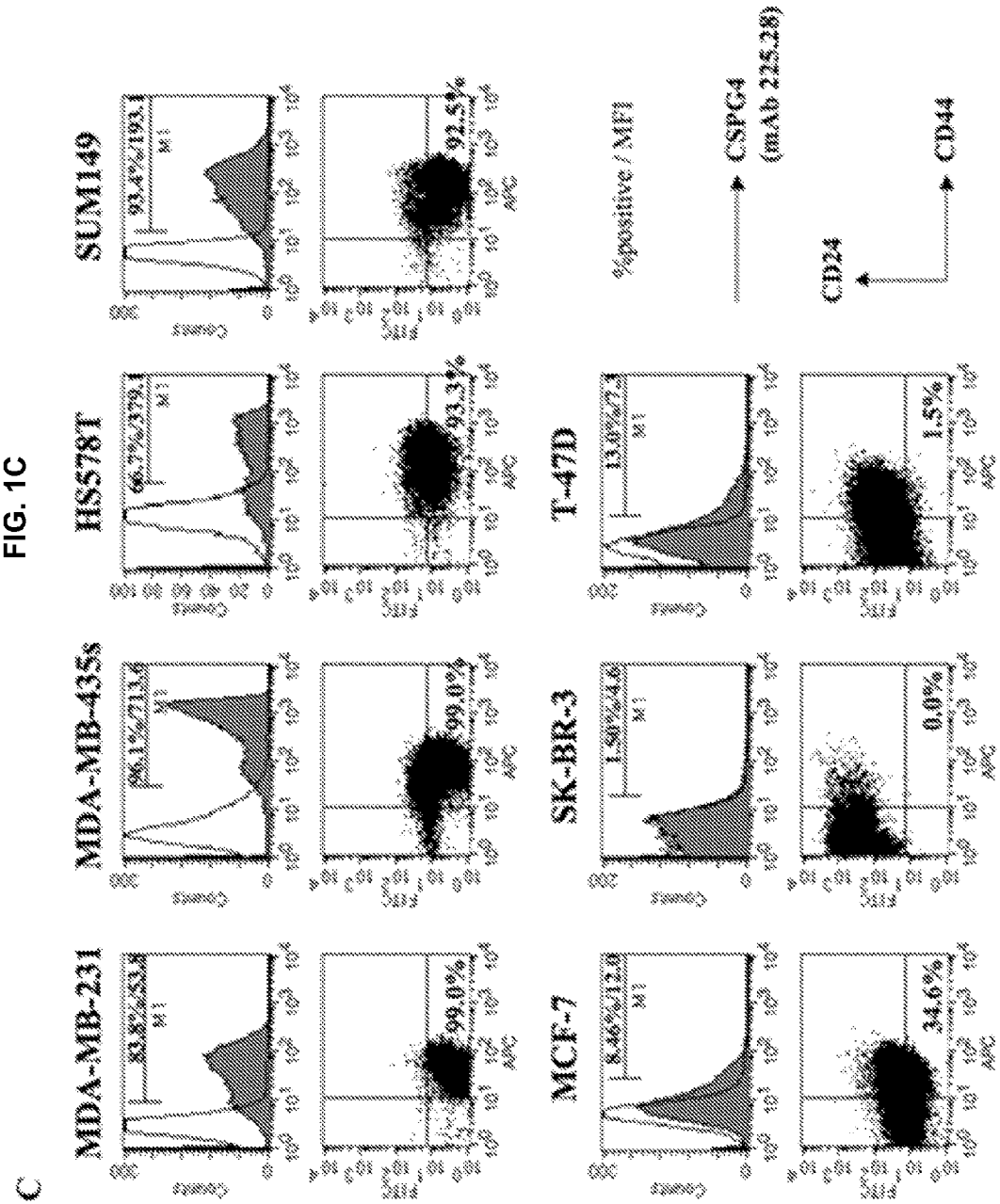

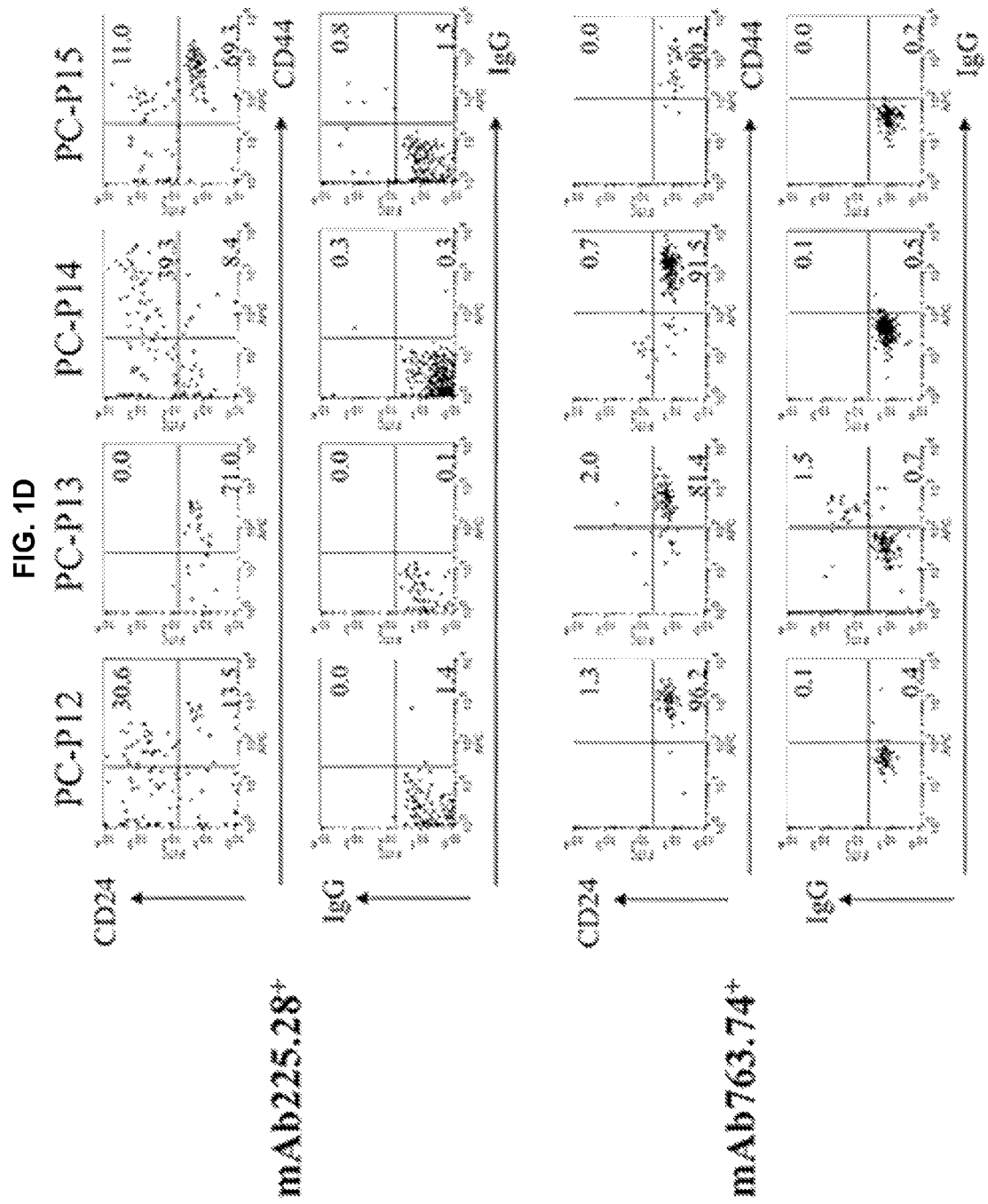

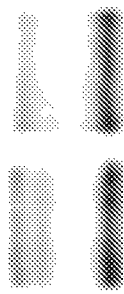
FIG. 6A
FIG. 6B
CSPG4
Loading control

MONOCLONAL ANTIBODIES FOR CSPG4 FOR THE DIAGNOSIS AND TREATMENT OF BASAL BREAST CARCINOMA

CROSS REFERENCE TO RELATED APPLICATION

This application is the U.S. National Stage of PCT Application No. PCT/US2009/057578, filed Sep. 18, 2009, which was published in English under PCT Article 21(2), which in turn claims the benefit of U.S. Provisional Application No. 61/098,548, filed Sep. 19, 2008, which is incorporated by reference herein in its entirety.

STATEMENT OF GOVERNMENT SUPPORT

This invention was made with government support under grant CA16056 and CA 105500 awarded by the National Cancer Institute, National Institutes of Health. The United States government has certain rights in the invention.

FIELD

This application relates to the field of breast cancer, specifically to methods for detecting and treating basal breast carcinoma.

BACKGROUND

Breast cancer is the most common type of epithelial cancer among women in the United States. More than 180,000 women are diagnosed with breast cancer each year. About 1 in 8 women in the United States (approximately 12.8 percent) will develop breast cancer during her lifetime. At present there are no curative therapies available for breast cancer that has metastasized from its site of origination. In addition, there is a need for diagnostic markers of use in the detection and staging breast cancers.

DNA microarray profiling of breast tumors has identified distinct subtypes with different clinical outcomes. They include normal breast-like, Her-2 overexpressing, luminal A and B (predominantly $ER^+$), and basal subtypes. Basal-like (referred to as basal) breast cancer (BBC), which includes the A and B subsets, is associated with high grade, poor prognosis, and younger patients. Because of the lack of estrogen, progesterone and epidermal growth factor (Her2) receptor expression, triple negative breast cancer (TNBC), which represents 15-20% of all breast cancer, is not suitable for Her2 targeted and/or anti-estrogen-based therapies. Furthermore, BBC is chemo- and radio-resistant. The resistance and aggressive behavior of this tumor may reflect its enrichment for cancer stem cells (CSC) that have the phenotype of $CD44^+$ and $CD24^{-/lo}$. CSC are chemo- and radio-resistant and responsible for metastatic spreading and disease recurrence. TNBC cell lines have "stem cell-like" gene expression and are classified as Basal B. A need remains for a method to detect and treat TNBC.

SUMMARY

It is disclosed herein that condroitin sulfate proteoglycan 4 (CSPG4), also known as high molecular weight melanoma associated antigen, is overexpressed on basal breast carcinoma cells (BBC), of the type also known as triple negative breast cancer cell (TNBC).

Methods for detecting basal breast cancer (BBC) and/or triple negative breast cancer in a subject are disclosed. These methods include selecting a subject with breast cancer or suspected of having breast cancer, and detecting the presence of CDPG4 in the sample. In one example, the method includes contacting a sample obtained from the subject with an antibody that specifically binds CSPG4 for a sufficient amount of time to form an immune complex, and detecting the presence of the immune complex, wherein the presence of an immune complex demonstrates the presence of breast cancer in the subject, such as BBC and/or TNBC.

Methods are also disclosed for inhibiting the growth of a basal breast cancer cell and/or a triple negative breast cancer cell. These methods include contacting the basal breast cancer cell and/or triple negative breast cancer cell with an effective amount of an antibody that specifically binds CSPG4, thereby inhibiting the growth of the cancer cell. These methods are of use to treat BBC, such as TNBC.

Additional treatment methods, and the use of more than one antibody, are also described herein.

The foregoing and other features and advantages will become more apparent from the following detailed description of several embodiments, which proceeds with reference to the accompanying figures.

BRIEF DESCRIPTION OF THE FIGURES

FIGS. 1A-1D are graphs and digital images showing preferential CSPG4 expression by TNBC. FIG. 1A is a graph showing an analysis of CSPG4 gene expression levels in published clinical microarray expression data sets (GSE5460) showed significantly higher levels in estrogen receptor $ER^-$, $Her^2$-breast cancers than in $ER-/Her2^+$, $ER^+/Her2^-$ and $ER^+/Her2^+$ breast cancers. FIG. 1B is a set of digital images of CSPG4 expression in TNBC lesions. Representative IHC staining of human TNBC lesions by CSPG4-specific mAb D2.8.5-C4B8 (3 µg/ml) is shown. The staining was graded as A. (−): no $CSPG4^+$ cells were detected; B. (+): less than 10% $CSPG4^+$ cells were detected; C (++): between 10-80% $CSPG4^+$ cells were detected and D (+++): more than 80% $CSPG4^+$ cells were detected. (×200) FIG. 1C is a set of plots showing differential CSPG4 expression and frequency of $CD44^+/CD24^{-/lo}$ cells in luminal and basal breast cancer/TNBC cell lines. Cells were sequentially incubated with CSPG4-specific mAb 225.28, PE-labeled anti-mouse IgG antibodies, and FITC-labeled anti-CD24, APC-labeled anti-CD44, and 7-AAD. Stained cells were subjected to FACS analysis. The percentage of cells stained by mAb 225.28 and the mean fluorescence intensity are shown in each histogram. mA low percentage (1.5-13%) of breast cancer cells stained by CSPG4-specific mAb 225.28 is associated with a low percentage (0-34.6%) of $CD44^+/CD24^{-/lo}$ cells in the three luminal type breast cancer cell lines (bottom panel). In contrast, a high percentage (66.7-96.1%) of breast cancer cells stained by CSPG4-specific mAb225.28 is associated with a high percentage (92.5-99.0%) of $CD44^+/CD24^{-/lo}$ cells in the 4 TNBC cell lines (top panel). FIG. 1D is a set of plots showing enrichment of putative CSC population in CSPG4+ cells in pleural effusions from patients with breast carcinoma. $7\text{-}AAD^-/CD45^-/CSPG4^+$ cells were analyzed for CD44/CD24 expression. The percentages of $CD44^+CD24^{-/lo}$ cells from four patient samples are shown in each dot plot.

FIGS. 2A and 2B are a set of digital images and a graph showing the inhibition of TNBC cell growth in vitro by CSPG4-specific mAb 225.28. MDA-MB-231 cells were treated either with mAb 225.28 or control mAb F3C25 in a 3-D (matrigel) setting for 6 days. The PBS, which was used as the solvent for both mAbs, was used as a reference for 100% cell growth. The pictures were taken under Zeiss Inverted Fluorescence Microscope (AxioVision Software) of each well (×100) (FIG. 2A) and cells in each well were then harvested from matrigel using Cell Recovery Solution (BD Pharmingen) and counted using Trypan Blue by two individuals. The results are expressed as % inhibition of cell growth, utilizing the values obtained in PBS only as a reference. The values shown are the mean of three independent experiments. * indicates p<0.001 (FIG. 2B). FIG. 2C is a graph showing the inhibition of TNBC cell adhesion by CSPG4-specific mAb 225.28. MDA-MB-435 cells were seeded and incubated with either CSPG4-specific mAb 225.28, isotype control mAb F3C25 or PBS in an adhesion assay. The results are expressed as % inhibition of adhesion, utilizing the values obtained in PBS without mAb as a reference. The values shown are the mean of three independent experiments. * indicates p<0.001. FIG. 2D is a graph showing the inhibition of TNBC cell migration by CSPG4-specific mAb 225.28. MDA-MB-231 cells were seeded and incubated with either CSPG4-specific mAb 225.28, control mAb F3C25 or PBS in a migration assay. The results are expressed as % inhibition of migration, utilizing the values obtained in PBS without mAb as a reference. The values shown are the mean of three independent experiments. *** indicates p<0.001.

FIGS. 4A and 4B show the inhibition by CSPG4-specific mAb of experimental metastases in vivo. Eight-week old female SCID mice were transplanted intravenously (i.v.) with MDA-MB-231 cells ($1\times10^6$) or MDA-MB-435 cells ($2\times10^6$) on day 0. On day 3, the mice bearing MDA-MB-231 derived metastases were divided into two groups. One was treated with CSPG4-specific mAb 225.28 (100 μg/i.v. injection) and one with control mAb F3C25 (100 μg/i.v. injection). The mice bearing MDA-MB-435 derived metastases were divided into three groups. One was treated with CSPG4-specific mAb 225.28 (100 μg/i.p. injection), one with CSPG4-specific mAb 763.74 (100 μg/i.p. injection), and one with control mAb (100 μg/i.p. injection). The injections were given twice weekly. The mice transplanted with MDA-MB-231 cells were euthanized on day 79 (FIG. 4A) and those transplanted with MDA-MB-435 cells on day 34 (FIG. 4B). Lungs were collected and fixed in Bouin's fixative (Polysciences). The lung metastases were counted under a dissecting microscope (Zeiss stemi DV4) and analyzed.  indicates p<0.01, * indicates p<0.001. FIGS. 4C, 4D and 4E are graphs and digital images showing regression by CSPG4-specific mAb of established experimental metastases in vivo. MDA-MB-231 cells ($1\times10^6$) were injected i.v. to 14 mice on day 0. Subsequently, all tumor bearing mice were randomized into two groups (7/group). Starting on day 20, one group was injected i.v. with CSPG4-specific mAb 225.28 (100 μg/mouse) and the other group was injected i.v. with the control mAb F3C25 (100 μg/mouse) every 48 hours for a total of three injections. On day 25, all mice were sacrificed and the lungs were collected and fixed in 10% formalin and paraffin-embedded for the following analysis: the sizes/areas of metastatic nodules (in randomly selected 5 high power fields (×200)/each section) were measured and calculated by the SPOT IMAGING SOFTWARE Advanced (Diagnostic Instruments, Inc.). The values shown are the mean tumor area of each group. * indicates p value<0.001 (FIG. 4C); the apoptotic tumor cells in lung tissue sections were detected by TUNEL assay and quantified by counting 10 fields/per slide (×200). The values shown are the mean apoptotic tumor cells of each group.  indicates p<0.01 (FIG. 4D) and the proliferating tumor cells in lung tissue sections were detected by staining p-Histone H3 protein and quantified by counting 10 fields/per slide (×200). The values shown are the mean mitotic tumor cells of each group. ** indicates p value<0.01 (FIG. 4E).

FIGS. 5A and 5B are graphs that show the inhibition by CSPG4-specific mAb of post-surgery tumor spontaneous metastases and recurrence in vivo. MDA-MB-435 cells ($2\times10^6$) were injected into a mammary fat pad of each SCID mouse on day 0. On day 7, when tumors were measurable, mice were divided into 3 groups of 5 mice each, such that the mean tumor volume in each group was similar (16 mm$^3$) Starting on day 7, one of the groups was injected i.p. with CSPG4-specific mAb 763.74 (100 μg/mouse) and one with CSPG4-specific mAb 225.28 (100 μg/mouse) twice weekly for a total of 18 injections. The third group of mice was injected with a control mAb (100 μg/mouse). On day 71, all tumors were removed surgically. The treatment with antibodies was continued using the same regimen with 9 additional injections. On day 131, all mice were sacrificed, and examined for lung metastases (FIG. 5A) and local tumor recurrence (FIG. 5B). This experiment was repeated twice. * indicates p value<0.05. FIGS. 5C and 5D are digital images and a graph showing inhibition of tumor angiogenesis and down regulation of in vivo signaling relevant to cell growth, adhesion and migration by CSPG4-specific mAb. The number of blood vessels in surgically removed MDA-MB-435 cell-derived primary tumors was detected by staining CD31 and quantified using five tumors from each group by capturing 5 random fields (×400) of each section. * indicates p value<0.05 (FIGS. 5C and 5D). Western blotting of PKC-α, p-FAK, FAK, p-Erk1/2, Erk1/2, p-Akt and Akt in surgically removed MDA-MB-435 cell-derived primary tumors obtained from 5 mice/group treated with mAb 225.28 and 5 mice/group treated with the isotype control mAb F3C25 (1 tumor sample/per mouse/per lane for both groups) (FIG. 5E). HLA class I antigens were used as loading controls.

FIGS. 6A-6B are digital images showing the molecular profile of CSPG4 expressed by MDA-MB-435 cells. Total RNA was extracted from MDA-MB-435 cells. A 439 bp cDNA fragment of CSPG4 (lanes 7 and 8) was synthesized by RT-PCR (Luo, W., et al., *Oncogene* 25, 2873-2884, 2006). The PCR product was analyzed using 1.5% agarose gel. The melanoma cell lines M14, which does not express CSPG4 (lanes 2 and 6), and M14/CSPG4, which express CSPG4 following transfection with a CSPG4 encoding plasmid DNA (lanes 3 and 7) were used as controls. The housekeeping gene β-actin (lanes 2, 3 and 4) was used as an internal control of RT-PCR. Lanes 1 and 5 are DNA molecular markers (FIG. 6A). A lysate from cells MDA-MB-435 (lanes 3 and 6) was separated by 8% SDS-PAGE for immunoblot analysis with CSPG4-specific mAb 763.74 (lanes 1-3). The isotype matched mAb MK2-23 (Kusama et al., *J Immunol* 143, 3844-3852 (1989) (lanes 4-6) and the M14 (lanes 1 and 4), and M14/CSPG4 cells (lanes 2 and 5) were used as controls. Calnexin (lanes 1-6), detected by mAb TO-5 (Ogino et al., *J Immunol Methods* 278, 33-44, 2003) was used as a loading control (FIG. 6B).

DETAILED DESCRIPTION

Sequence Listing

Figure 1A:
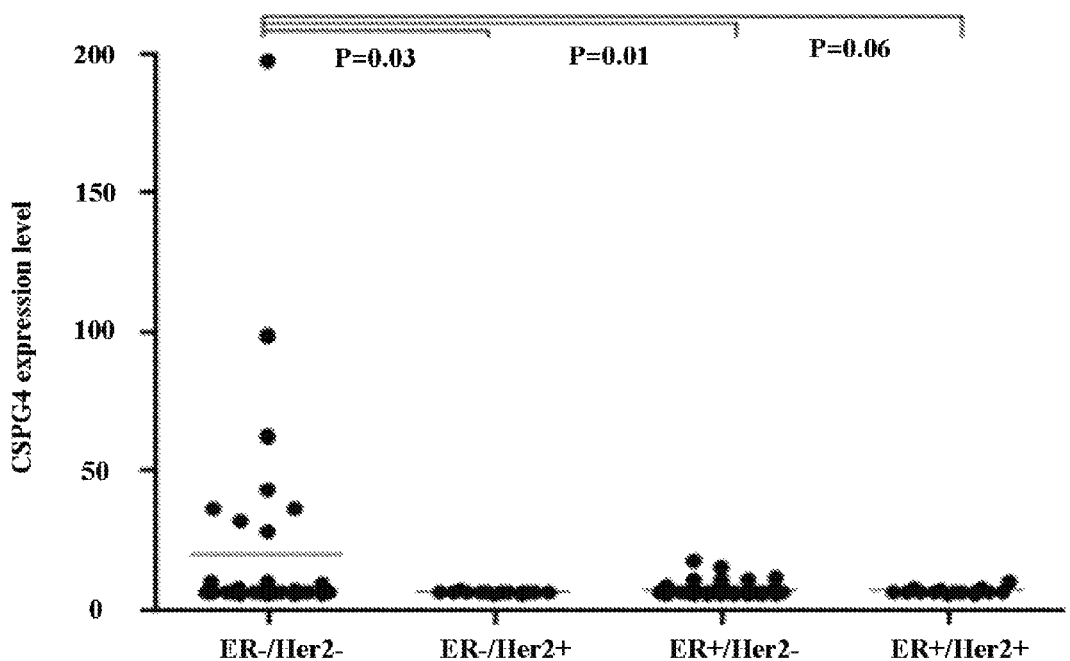

The Sequence Listing is submitted as an ASCII text file [8123-81756-07_sequence lisitng.txt, Mar. 16, 2011, 9.93 KB], which is incorporated by reference herein.

In the work described herein, DNA microarray profiles of triple negative breast cancer (TNBC) followed by immunohistochemistry (IHC) of different subtypes of human breast cancer tissues were analyzed to identify immunotherapeutic targets. This analysis showed the membrane bound chondroitin sulfate proteoglycan 4 (CSPG4), also known as high molecular weight-melanoma associated antigen (Campoli, M. R., et al., *Crit. Rev Immunol* 24, 267-296, 2004), to be predominantly expressed on TNBC cells. The cell lines used in the studies disclosed herein were defined as basal by DNA microarray (Neve, R M, et al. (2006), *Cancer Cell* 10: 515-527, incorporated by reference herein).

CSPG4, which is highly conserved through phylogenetic evolution, consists of an N linked 280 kDa glycoprotein and a 450 kDa chondroitin sulfate proteoglycan, both heterogeneous in the expression of determinants on melanoma cells. Because of its high expression with limited inter- and intrasesional heterogeneity in at least 80% of melanoma lesions and its restricted distribution in normal tissues, CSPG4 has been used as an immunotherapy target in melanoma patients. Its clinical significance is indicated by the beneficial effect of CSPG4-specific antibodies induced by CSPG4 mimics (Mittelman et al., *Proc Natl Acad Sci USA* 89, 466-470, 1992) on the clinical course of the disease. CSPG4 and it's rat homolog, NG2 (see, for example, Neve, R. M., et al., *Cancer Cell* 10, 515-527, 2006), with its role in cell motility and migration (see, for example, Burg et al., *Exp Cell Res* 235, 254-264, 1997), is important for tumor cell growth, survival and resistance to therapy. These pathways modulate intergrin function (for example, focal adhesion kinase (FAK)), growth and survival pathways (such as ERk 1, 2 and Akt). Furthermore, NG2 has been shown to stimulate the expression of functional c-Met by an epigenetic mechanism.

Triple negative breast cancer (TNBC) is the most common form of BBC that is clinically negative for expression of estrogen and progesterone receptors (ER/PR) and HER2 protein (see Carey, Oncology 22(11), available on the internet on Oct. 1, 2008, incorporated by reference herein). One characteristic of TNBCs is their ability to migrate and metastasize (Brabletz et al., *Nat Rev Cancer* 5, 744-749, 2005), such as to the brain. It is demonstrated herein that the CSPG4 protein is expressed on TNBC cells. Furthermore, CSPG4 is predominantly expressed on TNBC tissues from patients and highly expressed by a subpopulation of cells with the CSC phenotype both in TNBC cell lines and in malignant pleural effusions from patients with breast carcinoma.

A functional role of CSPG4 blockade is demonstrated herein. For example, in TNBC xenograft metastasis, it is shown herein that CSPG4-specific mAb significantly inhibited growth and caused regression of established metastasis. Without being limiting, results are presented in an experimental TNBC mouse model and significantly inhibited post-surgery tumor recurrence and lung metastases in an orthotopic TNBC mouse model. The examples describe the use of the TNBC cell lines MDA-MB-435 and MDA-MB-231 used in these two tumor models to generate xenograft tumor/metastasis, both of which display the breast CSC phenotype (CD44$^+$, CD24$^{-/lo}$) in 99% of cells. The molecular mechanisms of action in inhibiting tumor recurrence and metastasis mediated by CSPG4-specific mAb involve its ability to inhibit both phosphotidylinositol-3-kinase (PI3K)/PTEN/Akt and MAPK pathways signaling and tumor angiogenesis. Without being bound by theory, the findings are likely to reflect the inhibition of activation of PKC-α, FAK PI3K/Akt and Erk 1, 2 pathways, all of which are associated with the function of CSPG4. These results indicate that CSPG4 is an important target to apply antibody-based immunotherapy in TNBC.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. An exemplary antigen is CSPG4. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least three, and more usually, at least five or eight to ten amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a breast specific antigen, or a prostate specific antigen. A disease-specific antigen is expressed coincidentally with a disease process. Specific non-limiting examples of a disease-specific antigen are an antigen whose expression correlates with, or is predictive of, tumor formation, such as breast cancer (for example, BBC or TNBC). A disease specific antigen may be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals, including non-human primates. Similarly, the term "subject" includes both human and veterinary subjects.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction. Physiol Rev 76, 69-125 (1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted ER$^-$/HER2$^-$/PR$^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a CD44$^+$CD24$^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: ER$^-$/PR$^-$/HER2$^-$/CK5$^+$/EGFR$^+$.

The basaluminal subtype of human breast cancer is distinguished from classical basal-type tumors in that only a fraction of the cells are positive for basal cytokeratin 5 (<70%). In addition, 35% of basaluminal breast cancers display HER2 amplification or overexpression (Laakso et al, 2006, Clin. Cancer Res. 12:4185-4191). In one example, basaluminal subtype tumors can be characterized as ER$^-$/PR$^-$/HER2$^+$/CK5$^+$/EGFR$^+$.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating breast and/or prostate cancer. In one embodiment, a chemotherapeutic agent is radioactive compound. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., ® 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Combination chemotherapy is the administration of more than one agent to treat cancer, such as the administration of antibodies to CSPG4 in combination with a radioactive or chemical compound to a subject.

Conservative variants: "Conservative" amino acid substitutions are those substitutions that do not substantially affect or decrease an activity or antigenicity of CSPG4. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Degenerate variant: A polynucleotide encoding a CSPG4 polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the CSPG4 polypeptide encoded by the nucleotide sequence is unchanged.

Diagnostic: Identifying the presence or nature of a pathologic condition, such as, but not limited to, breast cancer or prostate cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as breast cancer (for example, BBC), or metastasis.

Epitope: An antigenic determinant. These are particular chemical groups or peptide sequences on a molecule that are antigenic, i.e. that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least five or eight to ten amino acids in a unique spatial conformation. Methods of determining spatial conformation of epitopes include, for example, x-ray crystallography and 2-dimensional nuclear magnetic resonance. See, e.g., *Epitope Mapping Protocols* in *Methods in Molecular Biology*, Vol. 66, Glenn E. Morris, Ed (1996).

Estrogen Receptor (ER): A receptor that is activated by the hormone 17β-estradiol (estrogen). The main function of the estrogen receptor is as a DNA binding transcription factor that regulates gene expression. Estrogen receptors are overexpressed in around 70% of breast cancer cases, referred to as "ER positive" or "ER$^+$." Therapy for ER$^+$ breast cancer involves selective estrogen receptor modulators (SERMS) which behave as ER antagonists in breast tissue or aromatase inhibitors. ER status is also used to determine sensitivity of breast cancer lesions to tamoxifen and aromatase inhibitors.$^L$ Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

HER2: Human Epidermal growth factor Receptor 2 (Her2) is also known as Her 2/neu (or ErbB-2, ERBB2). It is a member of the ErbB protein family (also known as the epidermal growth factor receptor family). HER2 has also been designated as CD340 (cluster of differentiation 340) and p185. HER2 is notable for its role in the pathogenesis of breast cancer and as a target of treatment. It is a cell membrane surface-bound receptor tyrosine kinase and is normally involved in the signal transduction pathways leading to cell growth and differentiation.

Approximately 15-20 percent of breast cancers have an amplification of the HER2 gene or overexpression of its protein product. Overexpression of this receptor in breast cancer has been associated with increased disease recurrence and worse prognosis. Because of its prognostic role, breast tumors are routinely checked for overexpression of HER2. Overexpression also occurs in other cancer such as ovarian cancer, stomach cancer, and biologically aggressive forms of uterine cancer, such as uterine serous endometrial carcinoma.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies, such as antibodies that specifically bind CSPG4.

Immunoconjugate: A covalent linkage of an effector molecule to an antibody. The effector molecule can be a toxin. Specific, non-limiting examples of toxins include, but are not limited to, abrin, ricin, *Pseudomonas* exotoxin (PE, such as PE35, PE37, PE38, and PE40), diphtheria toxin (DT), saporin, restrictocin, or modified toxins thereof, or other toxic agents that directly or indirectly inhibit cell growth or kill cells. For example, PE and DT are highly toxic compounds that typically bring about death through liver and heart toxicity in humans. PE and DT, however, can be modified into a form for use as an immunotoxin by removing the native targeting component of the toxin (e.g., domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody, such as an antibody that specifically binds CSPG4, is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen, such as CSPG4, from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. MHC binding prediction programs are available on the internet, such as ProPed-I, located on the Imtech website (Singh and Raghava, ProPred1: Prediction of promiscuous MHC class-I binding sites, *Bioinformatics*, 2003).

Immunogenic composition: A composition comprising an antigenic polypeptide, such as a CSPG4 polypeptide, that induces a measurable immune response against cells expressing the polypeptide, such as the CSPG4 polypeptide. The immune response can be a measurable CTL response against cells expressing CSPG4 polypeptide, or a measurable B cell response (such as production of antibodies that specifically bind CSPG4) against a CSPG4 polypeptide, such as BBC (TNBC) cells. It further refers to isolated nucleic acids encoding a CSPG4 polypeptide that can be used to express the CSPG4 polypeptide (and elicit an immune response against CSPG4). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, CSPG4 polypeptide, or nucleic acid encoding the polypeptide, can be readily tested for its ability to induce a CTL or B cell response by art-recognized assays.

Immunoglobulin (antibody): A protein including one or more polypeptides substantially encoded by immunoglobulin genes that specifically binds an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH— terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.*, 85:5879-5883, 1988; Bird et al., *Science* 242:423-426, 1988; Hood et al., *Immunology*, Benjamin, N.Y., 2nd ed., 1984; Hunkapiller and Hood, *Nature* 323:15-16, 1986).

An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089).

A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741, which are herein incorporated by reference).

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length, such as from 8 to ten amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

Peptide Modifications: CSPG4 polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a CSPG4 polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least ten bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is CSPG4 polypeptide.

Probes and primers: A probe comprises an isolated nucleic acid attached to a detectable label or reporter molecule. Primers are short nucleic acids, preferably DNA oligonucleotides, 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise 20, 25, 30, 35, 40, 50 or more consecutive nucleotides.

Progesterone receptor (PR): A receptor, also known as NR3C3 (nuclear receptor subfamily 3, group C, member 3), that is a steroid receptor that specifically binds progesterone. The progesterone receptor is not expressed on triple negative basal breast cancer cells.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancers or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells Purified: The term purified does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. Substantial purification denotes purification from other proteins or cellular components. In one embodiment, a preparation is purified (or isolated) such that the protein or peptide represents at least 50% (such as, but not limited to, 70%, 80%, 90%, 95%, 98% or 99%) of the total peptide or protein content of the preparation. The CSPG4 polypeptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologues or variants of a CSPG4 polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a CSPG4 polypeptide are typically characterized by possession of at least 75%, for example at least 80%, sequence identity counted over the full length alignment with the amino acid sequence of CSPG4 using the NCBI Blast 2.0, gapped blastp set to default parameters. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95%, depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a CSPG4 specific binding agent is an agent that binds substantially to a CSPG4 polypeptide. In one embodiment, the specific binding agent is a monoclonal or polyclonal antibody that specifically binds CSPG4.

Subject: Living multi-cellular vertebrate organisms, a category that includes both human and veterinary subjects, including human and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, often called "helper" T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocytes. In another embodiment, a CD8 cell is a suppressor T cell.

Therapeutically active polypeptide: An agent, such as a CSPG4 polypeptide that causes induction of an immune response, as measured by clinical response (for example increase in a population of immune cells, production of antibody that specifically binds CSPG4, or measurable reduction of tumor burden). Therapeutically active molecules can also be made from nucleic acids. Examples of a nucleic acid based therapeutically active molecule is a nucleic acid sequence that encodes a CSPG4 polypeptide, wherein the nucleic acid sequence is operably linked to a control element such as a promoter. Therapeutically active agents can also include organic or other chemical compounds. Therapeutically active agents can also include adjuvants.

The terms "therapeutically effective fragment of CSPG4" or "therapeutically effective variant of CSPG4" includes any fragment of CSPG4, or variant of CSPG4, that retains a function of CSPG4, or retains an antigenic epitope of CSPG4.

In one embodiment, a therapeutically effective amount of a fragment of CSPG4 is an amount used to generate an immune response, or to treat breast cancer, specifically BBC, in a subject. Specific, non-limiting examples are the N-terminal half of CSPG4 or the C-terminal half of CSPG4. Treatment refers to a therapeutic intervention that ameliorates a sign or symptom of breast or prostate cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Bind CSPG4

Antibodies have been produced that specifically bind CSPG4, including monoclonal antibodies. In one example, CSPG4 has an amino acid sequence set forth as:

```
                                              (SEQ ID NO: 1)
EQMREEPEAA  YRLIQGPQYG  HLLVGGRPTS  AFSQFQIDQG

EVVFAFTNFS  SSHDHFRVLA  LARGVNASAV  VNVTVRALLH

VWAGGPWPQG  ATLRLDPTVL  DAGELANRTG  SVPRFRLLEG

PRHGRVVRVP  RARTEPGGSQ  LVEQFTQQDL  EDGRLGLEVG

RPEGRAPGPA  GDSLTLELWA  QGVPPAVASL  DFATEPYNAA

RPYSVALLSV  PEAARTEAGK  PESSTPTGEP  GPMASSPEPA

VAKGGFLSFL  EANMFSVIIP  MCLVLLLLAL  ILPLLFYLRK

RNKTGKHDVQ  VLTAKPRNGL  AGDTETFRKV  EPGQAIPLTA

VPGQLFP
```

See also GENBANK® Accession No. AAI28111 incorporated herein by reference)

CSPG4 is a human melanoma-associated chondroitin sulfate proteoglycan that plays a role in stabilizing cell-substratum interactions during early events of melanoma cell spreading on endothelial basement membranes. CSPG4 represents an integral membrane chondroitin sulfate proteoglycan expressed by human malignant melanoma cells.

CSPG4 is also known as HMW-MAA. In vivo, it is present in a molecule that consists of two noncovalently associated glycopolypeptides. One has an apparent molecular weight of 280K, and the other has an apparent molecular weight greater than 440K. HMW-MAA is synthesized and expressed by human melanoma cells (Spiro, R. C. et al. F. Biol. Chem. 264:1779 (1989); Esko, J. D., et al., Science 241:1092, 1988). Proteoglycans are glycoproteins with glycosaminoglycan (GAG) polysaccharide chains covalently attached to the serine residue in their core. The CSPG4 core protein is initially translated as a precursor with a molecular mass of 240K with asparagine N-linked oligosaccharides of the high mannose type.

In another example, the CSPG4 is encoded by the nucleic acid sequence set forth as:

```
                                              (SEQ ID NO: 2)
gggagcagat  gagggaggag  ccagaggcag  cataccgcct catccaggga  ccccagtatg  ggcatctcct  ggtgggcggg cggcccacct  cggccttcag  ccaattccag  atagaccagg gcgaggtggt  ctttgccttc  accaacttct  cctcctctca tgaccacttc  agagtcctgg  cactggctag  gggtgtcaat gcatcagccg  tagtgaacgt  cactgtgagg  gctctgctgc atgtgtgggc  aggtgggcca  tggcccagg  gtgccaccct gcgcctggac  cccaccgtcc  tagatgctgg  cgagctggcc aaccgcacag  gcagtgtgcc  gcgcttccgc  ctcctggagg gaccccggca  tggccgcgtg  gtccgcgtgc  cccgagcag gacggagccc  gggggcagcc  agctggtgga  gcagttcact cagcaggacc  ttgaggacgg  gaggctgggg  ctggaggtgg gcaggccaga  ggggagggcc  cccggccccg  caggtgacag tctcactctg  gagctgtggg  cacagggcgt  cccgcctgct gtggcctccc  tggactttgc  cactgagcct  tacaatgctg cccggcccta  cagcgtggcc  ctgctcagtg  tccccgaggc agccagagag  cagcaccccc  acaggcgagc  caggccccat ggcatccagc  cctgagcccg  ctgtggccaa  gggaggcttc ctgagcttcc  ttgaggccaa  catgttcagc  gtcatcatcc ccatgtgcct  ggtacttctg  ctcctggcgc  tcatcctgcc cctgctcttc  tacctccgaa  aacgcaacaa  gacgggcaag catgacgtcc  aggtcctgac  tgccaagccc  cgcaacggcc tggctggtga  caccgagacc  tttcgcaagg  tggagccagg ccaggccatc  ccgctcacag  ctgtgcctgg  ccagttattt cca
```

See also GENBANK® Accession No. BC128110, incorporated herein by reference. Once of skill in the art can readily use a nucleic acid sequence to produce a polypeptide, such as CSPG4 using standard method in molecular biology (see, for example, *Molecular Cloning: A Laboratory Manual*, 2nd ed., vol. 1-3, ed. Sambrook et al., Cold Spring Harbor Laboratory Press, Cold Spring Harbor, N.Y., 1989).

Methods are disclosed herein can be used to detect and treat TNBC, including TNBC in the breast and TNBC that has metastasized to other organs. Methods can be designed that utilize nucleic acid techniques to detect the expression of CDPG4, such as PCR-based analysis, such as RT-PCT.

In some embodiments, the methods disclosed herein utilize antibodies, such as monoclonal or polyclonal antibodies, that specifically bind CSPG4 to form an immune complex. Exemplary antibodies of use are disclosed in PCT Publication No. WO 89/11296, which is incorporated by reference herein. These antibodies include antibodies that bind high molecular weight melanoma associated antigen (HMW-MAA), as the amino acid sequence of HMW-MAA is identical to CSPG4.

Exemplary antibodies of use include mouse monoclonal antibodies 225.28; 763.74; VF1-TP41.2; VT80.112; 653.25; 763.74; TP61.5 and T8-203 (see PCT Publication No. 89/11296; Drake et al., Cancer Immunol. Immunother. DOI 10: 1007, s00262-008-0567-5, 2008; Goto et al., Clin. Cancer Res. 14: 3401-3407, 2008, all incorporated by reference herein. Monoclonal antibodies 225.28 and 763.74 were deposited previously by another at the American Type Culture Collection (ATCC). Several hybridomas secreting antibodies that specifically bind CSPG4 were previously deposited by others in accordance with the Budapest Treaty). In one specific example, the antibody is monoclonal antibody (mAb) 225.28, or is a chimeric, humanized or fully human antibody that specifically binds the epitope bound by mAb 225.28. In a further embodiment, the antibody is a functional fragment of monoclonal antibody (mAb)) 225.28, a chimeric, humanized or fully human antibody that specifically binds the epitope bound by mAb 225.28. In another specific example, the antibody is mAb 763.74, or is a chimeric, humanized or fully human antibody that specifically binds the epitope bound by mAb 763.74. Similarly, the antibody can be a functional fragment of mAb 763.74, or a functional fragment of a chimeric, humanized or fully human antibody that specifically binds the epitope bound by mAb 763.74. In some embodiments, the antibodies are any fully human antibody that specifically binds CSPG4.

Chimeric, humanized and fully human antibodies, and antibody fragments, wherein these antibodies or fragments specifically bind CSPG4, are of use in the methods disclosed herein. A panel of different antibodies that bind different epitopes, and/or functional fragments of these antibodies, can also be used in any of the methods disclosed herein. Thus, the disclosed methods can include the use of one, two, three, four, five or six antibodies, or functional fragments thereof, that specifically bind CSPG4.

Humanized monoclonal antibodies are produced by transferring donor antibody (from an antibody disclosed herein) complementarity determining regions from heavy and light variable chains of the mouse immunoglobulin into a human variable domain, and then substituting human residues in the framework regions of the donor counterparts. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, U.S. Pat. No. 5,585,089).

Antibodies include intact molecules as well as fragments thereof, such as Fab, F(ab')$_2$, and Fv which include a heavy chain and light chain variable region and are capable of specifically binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. An exemplary scFV that specifically binds CSPG4 is scFv-Fc C21; a scFV fragment can be used in any of the methods disclosed herein.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

In one example, the variable region included in the immunotoxin is an Fv, which includes the variable region of the light chain and the variable region of the heavy chain expressed as individual polypeptides. Fv antibodies are typically about 25 kDa and contain a complete antigen-binding site with 3 CDRs per each heavy chain and each light chain. The $V_H$ and the $V_L$ can be expressed from two individual nucleic acid constructs. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

One of skill in the art will realize that conservative variants of the antibodies can be produced. Such conservative variants employed in dsFv fragments or in scFv fragments will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. U.S.A.* 69:2659, 1972). Alternatively, the variable chains can be linked by an intermolecular disulfide bond or cross-linked by chemicals such as glutaraldehyde. See, e.g., Sandhu, supra. Thus, a dsFv can be produced. In an additional example, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., Bio/Technology 11:1271, 1993; and Sandhu, supra).

In some embodiments, the disclosed method utilize immunoconjugates. Immunoconjugates include, but are not limited to, molecules in which there is a covalent linkage of a diagnostic or therapeutic agent with an antibody. A therapeutic agent is an agent with a particular biological activity directed against a particular target molecule or a cell bearing a target molecule. Therapeutic agents include various drugs such as vinblastine, daunomycin and the like, and effector molecules such as cytotoxins such as native or modified *Pseudomonas* exotoxin or Diphtheria toxin, encapsulating agents (e.g., liposomes), which themselves contain pharmacological compositions, target moieties and ligands.

The choice of a particular therapeutic agent depends on the particular target molecule or cell and the biological effect desired. Thus, for example, the therapeutic agent may be an effector molecule that is cytotoxin which is used to bring about the death of a particular target cell. Conversely, where it is merely desired to invoke a non-lethal biological response, a therapeutic agent can be conjugated to a non-lethal pharmacological agent or a liposome containing a non-lethal pharmacological agent.

Toxins can be employed with antibodies that bind the any extracellular portion of a CSPG4 polypeptide and fragments, such as a svFv or a dsFv, to yield chimeric molecules, which are of use as immunotoxins. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, *J. Virol.* 19:220, 1976), and has been used in human clinical trials. See, U.S. Pat. No. 5,792,458 and U.S. Pat. No. 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat Biotech* 17:265-270, 1999). Exemplary ribotoxins such as α-sarcin and restrictocin are discussed in, e.g., Rathore et al., *Gene* 190:31-35, 1997; and Goyal and Batra, *Biochem* 345 Pt 2:247-254, 2000. Calicheamicins were first isolated from *Micromonospora echinospora* and are members of the enediyne antitumor antibiotic family that cause double strand breaks in DNA that lead to apoptosis (see, e.g., Lee et al., *J. Antibiot* 42:1070-1087. 1989). The drug is the toxic moiety of an immunotoxin in clinical trials (see, e.g., Gillespie et al., *Ann Oncol* 11:735-741, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu et al., *Agr. Biol. Chem.* 52:1095, 1988; and Olsnes, *Methods Enzymol.* 50:330-335, 1978).

In one embodiment, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence and the sequence of modified PE are provided in U.S. Pat. No. 5,602,095, incorporated herein by reference. In one embodiment, native PE has a sequence set forth as:

```
                                          (SEQ ID NO: 3)
AEEAFDLWNE  CAKACVLDLK  DGVRSSRMSV  DPAIADTNGQ

GVLHYSMVLE  GGNDALKLAI  DNALSITSDG  LTIRLEGGVE

PNKPVRYSYT  RQARGSWSLN  WLVPIGHEKP  SNIKVFIHEL

NAGNQLSHMS  PIYTIEMGDE  LLAKLARDAT  FFVRAHESNE

MQPTLAISHA  GVSVVMAQTQ  PRREKRWSEW  ASGKVLCLLD

PLDGVYNYLA  QQRCNLDDTW  EGKIYRVLAG  NPAKHDLDIK

PTVISHRLHF  PEGGSLAALT  AHQACHLPLE  TFTRHRQPRG

WEQLEQCGYP  VQRLVALYLA  ARLSWNQVDQ  VIRNALASPG

SGGDLGEAIR  EQPEQARLAL  TLAAAESERF  VRQGTGNDEA

GAANADVVSL  TCPVAAGECA  GPADSGDALL  ERNYPTGAEF

LGDGGDVSFS  TRGTQNWTVE  RLLQAHRQLE  ERGYVFVGYH

GTFLEAAQSI  VFGGVRARSQ  DLDAIWRGFY  IAGDPALAYG

YAQDQEPDAR  GRIRNGALLR  VYVPRSSLPG  FYRTSLTLAA

PEAAGEVERL  IGHPLPLRLD  AITGPEEEGG  RLETILGWPL

AERTVVIPSA  IPTDPRNVGG  DLDPSSIPDK  EQAISALPDY

ASQPGKPPRE  DLK
```

The method of action of PE is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall et al., *J. Biol. Chem.* 264:14256-14261, 1989.

The term "*Pseudomonas* exotoxin" ("PE") as used herein refers as appropriate to a full-length native (naturally occurring) PE or to a PE that has been modified. Such modifications may include, but are not limited to, elimination of domain Ia, various amino acid deletions in domains Ib, II and III, single amino acid substitutions and the addition of one or more sequences at the carboxyl terminus, such as KDEL (SEQ ID NO: 4) and REDL (SEQ ID NO: 5) (see Siegall et al., supra). In several examples, the cytotoxic fragment of PE retains at least 50%, such as about 75%, about 90%, or about 95% of the cytotoxicity of native PE. In one embodiment, the cytotoxic fragment is more toxic than native PE.

Thus, the PE used in the immunotoxins disclosed herein includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE known in the art include PE40, PE38, and PE35.

In several embodiments, the PE has been modified to reduce or eliminate non-specific cell binding, typically by deleting domain Ia, as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E") exhibits greatly diminished non-specific cytotoxicity. This mutant form of PE is sometimes referred to as PE4E. PE40 is a truncated derivative of PE (see, Pai et al., *Proc. Nat'l Acad. Sci. U.S.A.* 88:3358-3362, 1991; and Kondo et al., *J. Biol. Chem.* 263:9470-9475, 1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. No. 5,602,095 and U.S. Pat. No. 4,892,827.

In some embodiments, the cytotoxic fragment PE38 is employed. PE38 is a truncated PE pro-protein composed of amino acids 253-364 and 381-613 of SEQ ID NO: 3 which is activated to its cytotoxic form upon processing within a cell (see e.g., U.S. Pat. No. 5,608,039, and Pastan et al., *Biochim. Biophys. Acta* 1333:$C_1$-$C_6$, 1997).

While in some embodiments, the PE is PE4E, PE40, or PE38, any form of PE in which non-specific cytotoxicity has been eliminated or reduced to levels in which significant toxicity to non-targeted cells does not occur can be used in the immunotoxins disclosed herein so long as it remains capable of translocation and EF-2 ribosylation in a targeted cell.

Conservatively modified variants of PE or cytotoxic fragments thereof have at least about 80% sequence identity, such as at least about 85% sequence similarity, at least about 90% sequence identity, or at least about 95% sequence similarity at the amino acid level, with the PE of interest, such as PE38.

With the antibodies and immunotoxins herein provided, one of skill can readily construct a variety of clones containing functionally equivalent nucleic acids, such as nucleic acids which differ in sequence but which encode the same effector molecule ("EM") or antibody sequence. Thus, nucleic acids encoding antibodies and conjugates and fusion proteins are provided herein.

Nucleic acid sequences encoding the immunotoxins can be prepared by any suitable method including, for example, cloning of appropriate sequences or by direct chemical synthesis by methods such as the phosphotriester method of Narang, et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, e.g., using an automated synthesizer as described in, for example, Needham-VanDevanter et al. *Nucl. Acids Res.* 12:6159-6168, 1984; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In one embodiment, the nucleic acid sequences encoding the immunotoxin are prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an immunotoxin of use is prepared by inserting the cDNA which encodes a variable region into a vector which comprises the cDNA encoding the EM. The insertion is made so that the variable region and the EM are read in frame so that one continuous polypeptide is produced. The polypeptide contains a functional Fv region and a functional EM region. In one embodiment, cDNA encoding a cytotoxin is ligated to a scFv so that the cytotoxin is located at the carboxyl terminus of the scFv. In one example, cDNA encoding a Pseudomonas exotoxin ("PE"), mutated to eliminate or to reduce non-specific binding, is ligated to a scFv so that the toxin is located at the amino terminus of the scFv. In another example, PE38 is located at the amino terminus of the scFv (such as scFv-Fc C21). In a further example, cDNA encoding a cytotoxin is ligated to a heavy chain variable region of an antibody that binds the antigen of interest so that the cytoxin is located at the carboxyl terminus of the heavy chain variable region. The heavy chain-variable region can subsequently be ligated to a light chain variable region of the antibody using disulfide bonds. In yet another example, cDNA encoding a cytotoxin is ligated to a light chain variable region of an antibody that binds the antigen (for example, CSPG4), so that the cytotoxin is located at the carboxyl terminus of the light chain variable region. The light chain-variable region can subsequently be ligated to a heavy chain variable region of the antibody using disulfide bonds.

Once the nucleic acids encoding the immunotoxin is isolated and cloned, the protein can be expressed in a recombinantly engineered cell such as bacteria, plant, yeast, insect and mammalian cells. One or more DNA sequences encoding an immunotoxin can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the immunotoxin can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the immunotoxin can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as $E.$ $coli$, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the immunotoxin, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide may be carried out by conventional means including preparative chromatography and immunological separations. Once expressed, the recombinant immunotoxins can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as $E.$ $coli$ have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from $E.$ $coli$ or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. It is desirable to add excess oxidized glutathione or other oxidizing low molecular weight compounds to the refolding solution after the redox-shuffling is completed.

In addition to recombinant methods, the immunoconjugates, EM, and antibodies disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (e.g., by the use of the coupling reagent N,N'-dicyclohexylcarbodiimide) are well known in the art.

Pharmaceutical Compositions and Therapeutic Methods Using Antibodies

Compositions including an antibody that specifically bind CSPG4, as disclosed above, can be used for the treatment of basal breast carcinoma (BBC). In one example, methods are disclosed herein for the treatment of triple negative basal breast cancer (TNBC), which do not express estrogen, progesterone, or Her2. Thus, compositions comprising a therapeutically effective amount of an antibody that specifically binds CSPG4 for use in treating BBC, such as TNBC, are provided herein. In one example, the BBC (such as a TNBC) is metastatic. In additional embodiments, method are provided for treating colon, ovarian, breast, prostate, lung or pancreatic cancer.

In one embodiment, the method includes selecting a subject diagnosed with BBC (such as a TNBC), and administering to the subject a therapeutically effective amount of an antibody that specifically binds CSPG4. In one example, the method includes selecting a subject with metastatic BBC, such as a metastatic TNBC.

In further embodiments methods are provided for inhibiting the growth and/or metastasis of a cancer cell. The cancer cell can be a colon, ovarian, breast, prostate, lung or pancreatic cancer cell. The cancer cell can be a BBC cell. The cancer cell can be a TNBC cell. The cell can be in vivo or in vitro.

The antibody can be any antibody that specifically binds CSPG4, such as those described herein. Thus, the antibody can be, but is not limited to, a monoclonal antibody, a humanized antibody, a fully human antibody, or a functional fragment of an antibody, provided that the antibody specifically binds CSPG4. Combinations of these agents can also be utilized in the disclosed methods.

In some non-limiting examples, the antibody is mAb 225.28, 763.74, TP41.2 or TP61.5, a humanized for thereof or a functional fragment thereof that specifically binds CSPG4. In another non-limiting example the antibody is scFv-Fc C21. These antibodies can be used in alone or in any combination. In some embodiments, the antibody is bound to a toxin.

Compositions including the antibodies disclosed herein can be prepared in unit dosage forms for administration to a subject. The amount and timing of administration are at the discretion of the treating physician to achieve the desired purposes. In one example, an antibody or immunotoxin is formulated for parenteral administration, such as intravenous administration. In other examples, the antibody or immunotoxin is formulated for systemic or local (such as intra-tumor) administration. These compositions are of use in treating subjects with breast cancer, such as BBC (for example, TNBC). Thus, the methods disclosed herein include selecting a subject with a BBC such as a TNBC. The methods can also include identifying a subject with BBC, and/or identifying a subject with TNBC, using an antibody that specifically binds CSPG4, as disclosed below, and then treating the subject. In some examples, the BBC is metastatic BBC, such as a metastatic TNBC. In some examples, the method is a method for treating BBC, such as a TNBC in a subject.

The compositions for therapeutic administration will commonly comprise a solution of the antibody, such as an immunotoxin, dissolved in a pharmaceutically acceptable carrier, such as an aqueous carrier, for administration to a subject with breast cancer, such as BBC (for example, TNBC). A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The antibodies, such as can be administered to slow or inhibit the growth of cells that express the antigen (CSPG4), such as BBC cells, for example TNBC cells. In these applications, a therapeutically effective amount of an antibody that binds CSPG4, for example an immunotoxin, is administered to a subject in an amount sufficient to inhibit growth of antigen-expressing cells, such as BBC (TNBC) cells. Suitable subjects include those with a breast cancer that expresses a CSPG4, such as a subject with BBC, for example TNBC. Suitable subjects also include those with a metastatic cancer thought to be BBC, and/or with a metastatic cancer thought to be TNBC.

A typical pharmaceutical of an antibody, such as an immunotoxin composition, for intravenous administration includes about 0.1 to 10 mg per patient per day. Dosages from 0.1 up to about 100 mg per patient per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19*th ed*., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% Sodium Chloride, USP, and typically administered at a dosage of from 0.5 to 15 mg/kg of body weight. Considerable experience is available in the art in the administration of antibody drugs, which have been marketed in the U.S. since the approval of Rituxan® in 1997. Antibody drugs can be administered by slow infusion, rather than in an IV push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Single or multiple administrations of the compositions are administered depending on the dosage and frequency as required and tolerated by the subject. In any event, the composition should provide a sufficient quantity of at least one of the antibodies disclosed herein to effectively treat the patient with breast cancer (e.g. BBC). The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Amounts effective for this use will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Controlled release parenteral formulations of the compositions including the antibody can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., *Colloidal Drug Delivery Systems*, J. Kreuter, ed., Marcel Dekker, Inc., New York, N.Y., pp. 219-342, 1994; and Tice & Tabibi, *Treatise on Controlled Drug Delivery*, A. Kydonieus, ed., Marcel Dekker, Inc. New York, N.Y., pp. 315-339, 1992, both of which are incorporated herein by reference.

Polymers can be used for ion-controlled release of the antibody or immunoconjugate compositions disclosed herein. Various degradable and nondegradable polymeric matrices for use in controlled drug delivery are known in the art (Langer, *Accounts Chem. Res.* 26:537-542, 1993). For example, the block copolymer, poloxamer 407, exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known. See, e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496, each of which is incorporated herein by reference.

A therapeutically effective amount of an antibody will depend upon the severity of the disease and the general state of the patient's health. A therapeutically effective amount of the antibody is that which provides either subjective relief of a symptom(s) or an objectively identifiable improvement as noted by the clinician or other qualified observer.

In some embodiments, the antibody that specifically binds CSPG4 is administered with other agents, such as chemotherapeutic agents, either simultaneously or sequentially. Many chemotherapeutic agents are presently known in the art. Thus, the method can include administering a therapeutically effective amount of an antibody that specifically binds CSPG4 and a therapeutically effective amount of a chemotherapeutic agent. In several embodiments, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of anti-metabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocortical suppressants (such as mitotane and aminoglutethimide). Examples of hormones and antagonists include adrenocorticosteroids (such as prednisone), progestins (such as hydroxyprogesterone caproate, medroxyprogesterone acetate, and megestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs that can be concurrently administered with the disclosed immunotherapy include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

In several specific non-liming examples, a therapeutically effective amount of ABRAXANE® (paclitaxel protein-bound particles for injectable suspension), ADRIAMYCIN® (doxorubicin), AREDIA® (generic name, pamidronate disodium), ARIMIDEX® (anastrozole), AROMASIN® (exemestane), CYTOXAN® (cyclophosphamide), ELLENCE® (epirubicin), EVISTA® (raloxifene), FARESTON® (toremifene), FEMARA® (letrozole), HERCEPTIN® (trastuzumab), MEGACE® (megestrol), Tamoxifen, TAXOL® (paclitaxel), TAXOTERE® (docetaxel), XELODA® (capecitabine), ZOLADEX® (goserelin acetate), and/or ZOMETA® (generic name, zoledronic acid) is administered.

Diagnosis of Basal Breast Carcinoma

It is disclosed herein that CSPG4 is differentially expressed in human breast cancers. Specifically CSPG4 is expressed in BBC (specifically TNBC), which is often chemo- and radio-resistant. CSPG4 is expressed in cancer stem cells (CSC). Thus, expression of a CSPG4 polypeptide can be used to diagnose BBC (TNBC), can be used to stage breast cancer, or can be used to determine the prognosis of a subject with breast cancer, such as BBC, for example TNBC. Thus, the use of an antibody that specifically binds CSPG4 for the diagnosis of BBC, such as TNBC, is disclosed herein. In some embodiments, the method determines if the subject has BBC, such as a TNBC, as compared to another form of breast cancer. The method of diagnosis can be used to determine if a metastasis, such as a brain metastasis, is a BBC, such as a TNBC.

A method is provided herein for the detection of the expression of a CSPG4 polypeptide in cells or tissue by analyzing expression of the polypeptide in a biological sample. The sample can be any sample, including, but not limited to, tissue from biopsies, autopsies, and pathology specimens. Biological samples also include sections of tissues, such as frozen sections taken for histological purposes. Biological samples further include body fluids, such as blood, serum, or urine. In one example, the biological sample is a breast tissue sample. In another embodiment, the biological sample is a sample of a tissue from another organ (not the breast), so that the presence of metastatic breast cancer is determined, such as in a brain biopsy. The biological sample is typically obtained from a mammal, such as a rat, mouse, cow, dog, guinea pig, rabbit, or primate, such as a human.

In a further embodiment, the subject has cancer, or is suspected of having cancer, such as breast cancer. In one example, the breast cancer is BBC, such as TNBC.

A method is also provided herein for detecting CSPG4 in a biological sample. The method includes contacting the sample with one or more of an antibody that specifically binds CSPG4 to form an antibody-CSPG4 complex. The presence or absence of the complex is detected. The methods are of use to improve the confidence of a tissue diagnosis, such as BBC (for example, TNBC), such as to confirm a diagnosis, or to determine the origin of a tumor. Thus, the method disclosed herein can be used to confirm the diagnosis of the BBC, such as TNBC.

The methods can include selecting a subject in need of diagnosis, such as a subject with a breast cancer or suspected of having breast cancer (such as a subject identified using mamography), and obtaining a sample from this subject. In several examples, the methods include selecting a subject with breast cancer, and using the methods disclosed herein to determine if the breast cancer is a BBC, such as a TNBC.

Antibodies that specifically bind CSPG4 are used in the methods disclosed herein. Antibodies include polyclonal and monoclonal antibodies, humanized and chimeric antibodies, as well as fully human antibodies. In some embodiments, an antibody fragment, wherein the antibody fragment specifically binds CSPG4 is utilized in these methods. In one example, the antibody fragment is an Fv fragment. In a further embodiment, the antibody is labeled (such as with a fluorescent, radioactive, or an enzymatic label). In additional examples, the antibodies can be conjugated to compounds including, but not limited to, enzymes, magnetic beads, colloidal magnetic beads, haptens, fluorochromes, metal compounds or radioactive compounds. Methods for labeling antibodies are well known in the art.

Methods of determining the presence or absence of a protein are well known in the art. Assays of use include, but are not limited to, radioimmunoassays (RIAs), enzyme linked immunosorbant assays (ELISA), or immunohistochemical assays. The method for detecting CSPG4 in a biological sample generally includes the steps of contacting the biological sample with an antibody which specifically reacts, under immunologically reactive conditions, to CSPG4. The antibody is allowed to specifically bind under immunologically reactive conditions to form an immune complex, and the presence of the immune complex (bound antibody) is detected directly or indirectly. A control cell, such as a non-transformed cell or section of the same tissue type, can be included as a control.

In one embodiment, a method is provided for detecting a polypeptide in a sample. Kits for detecting a polypeptide will typically comprise an antibody that specifically binds the CSPG4. The antibody can be a monoclonal antibody, a chimeric antibody, a humanized antibody, or a human antibody that specifically binds CSPG4. In some embodiments, an antibody fragment, such as an Fv fragment is included in the kit. For in vivo uses, the antibody can be a scFv fragment or a human antibody. In a further embodiment, the antibody is directly labeled (e.g. fluorescent, radioactive, or an enzymatic label).

In one embodiment, a kit includes instructional materials disclosing means of use of an antibody that specifically binds CSPG4 (e.g. for detection of BBC, such as TNBC, cells expressing CSPG4). The instructional materials may be written, in an electronic form (e.g. computer diskette or compact disk) or may be visual (e.g. video files). The kits may also include additional components to facilitate the particular application for which the kit is designed. Thus, for example, the kit may additionally contain means of detecting a label (e.g. enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay, such as an immunoassay to detect or stage a BBC, such as a TNBC. Although the details of the immunoassays may vary with the particular format employed, the method of detecting CSPG4 in a biological sample generally comprises the steps of contacting the biological sample with an antibody which specifically reacts, under immunologically reactive conditions, to the CSPG4 polypeptide. The antibody is allowed to specifically bind under immunologically reactive conditions to form an immune complex, and the presence of the immune complex (bound antibody) is detected directly or indirectly.

The methods also include detecting a nucleic acid in a sample, wherein the nucleic acid encodes CSPG4. Suitable methods are well known in the art. For example, samples from a subject can be tested to determine whether nucleic acids encoding CSPG4 are present. In one embodiment, an amplification procedure is utilized to detect nucleic acids encoding CSPG4, such as reverse transcriptase polymerase chain reaction (RT-PCR). In another embodiment, a blotting procedure (e.g. Northern Blot or Dot Blot) is used to detect the presence of nucleic acids encoding CSPG4. Thus, probes or primers that specifically hybridize to nucleic acids encoding CSPG4 are used to detect the presence of a BBC, such as a TNBC.

In an alternative set of embodiments, kits can be provided for detecting nucleic acids encoding CSPG4 in a biological sample. For example, a sample from a subject can be tested to determine whether nucleic acids encoding CSPG4 polypeptide are present, such as mRNA encoding a CSPG4 polypeptide. In one embodiment, an amplification procedure is utilized to detect nucleic acids encoding CSPG4. In another embodiment, a blotting procedure (e.g. Northern Blot or Dot Blot) is used to detect the presence of nucleic acids. In a further embodiment, nucleic acids of interest are amplified, and these nucleic acids are sequenced to determine if a CSPG4 polypeptide is expressed. Thus, a kit can include probes or primers that specifically hybridize under stringent conditions, or highly stringent conditions, to nucleic acids encoding CSPG4.

In one embodiment, a kit provides a primer that amplifies nucleic acid encoding CSPG4. Conveniently, the amplification is performed by polymerase chain reaction (PCR). A number of other techniques are, however, known in the art and are contemplated for use. For example, Marshall, U.S. Pat. No. 5,686,272, discloses the amplification of RNA sequences using ligase chain reaction, or "LCR," (Landegren et al., *Science* 241:1077, 1988); Wu et al., *Genomics* 4:569, 1989; Barany, in *PCR Methods and Applications* 1:5, 1991); and Barany, *Proc. Natl. Acad. Sci. U.S.A.* 88:189, 1991). Or, the RNA can be reverse transcribed into DNA and then amplified by LCR, PCR, or other methods. An exemplary protocol for conducting reverse transcription of RNA is taught in U.S. Pat. No. 5,705,365. Selection of appropriate primers and PCR protocols are taught, for example, in Innis et al., eds., *PCR Protocols*, 1990 (Academic Press, San Diego, Calif.). The resultant nucleic acids can be sequenced, or can be identified using specific CSPG4 probes using hybridization and blotting techniques well known in the art.

In one embodiment, the kit includes instructional materials disclosing means of use for the primer or probe. The kits may also include additional components to facilitate the particular application for which the kit is designed. The kits may additionally include buffers and other reagents routinely used for the practice of a particular method. Such kits and appropriate contents are well known to those of skill in the art.

Use of CSPG4 to Induce an Immune Response to Basal Breast Carcinoma

In one embodiment, methods are provided for producing an immune response to a CSPG4 polypeptide. The method is of use, for example, for the treatment of cancer, such as by reducing the growth of the cancer or reducing a sign or a symptom of the cancer in a subject. The cancer can be a breast cancer, such as a BBC, for example TNBC. The method includes administering to a subject a therapeutically effective amount of a polypeptide including the CSPG4 polypeptide, or a fragment thereof. The method can also include administering to a subject a nucleic acid encoding this polypeptide.

In one embodiment, the method includes administering a therapeutically effective amount of CSPG4 polypeptide in a pharmacologically acceptable carrier. In additional embodiment, the method includes administering to a subject an isolated immunogenic epitope of CSPG4. The immunogenic epitope can induce a B cell response and/or a T cell response. The use of nucleic acids encoding these polypeptides and epitopes for the treatment of basal breast cancer are also envisioned. The use of such an epitope can result in the production of antibodies and/or can result in a T cell response, such as the activation of T cells or the production of cytokines.

The presentation of peptides by MHC Class I molecules involves binding to the cleft in an MHC Class I molecule through the anchor residues of the peptide and ultimate presentation on the cell surface. Depending upon the particular anchor residues, among other things, certain peptides may bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to CTL cells. HLA A, HLA B and HLA C molecules bind peptides of about 8 to 10 amino acids in length that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In one example, the polypeptides disclosed herein bind and are presented by HLA-A2.1. Using the amino acid sequences for CSPG4, one of skill in the art can use a computer program to identify epitopes that will stimulate T cells. Such programs are publicly available on the internet, for example ProPed-I, which is available at the Imtech website. Fusion proteins including CSPG4 polypeptides, or immunogenic epitopes thereof, can also be utilized. For example, the CSPG4 polypeptide can be fused to an immunoglobulin polypeptide, glutathione-S-transferase, poly-histidine, or beta-galactosidase.

The subject can be any subject of interest. In one embodiment, the subject has breast cancer, specifically BBC, such as TNBC. Additional agents can be included, such as, but not limited to, chemotherapeutic agents or adjuvants. The method can include identifying and or selecting a subject with a BBC, such as a TNBC. In one embodiment, the CSPG4 polypeptide, or fragment or epitope thereof, is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN™) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977; and Hunter, et al. *J. Immunol.* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, such as in an amount between 1.25 and 5%.

The oil included in the composition is chosen to promote the retention of the antigen in oil-in-water emulsion, i.e., to provide a vehicle for the desired antigen, and can have a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, such as between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.). To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle (see, e.g., Banga, supra). A particulate carrier based on a synthetic polymer has been shown to act as an adjuvant to enhance the immune response, in addition to providing a controlled release. Aluminum salts may also be used as adjuvants to produce a humoral immune response. Thus, in one embodiment, the polypeptide is administered in a manner to induce a humoral response.

A CSPG4 polypeptide, fragment thereof, or immunogenic epitope, or nucleic acid endocing these polypeptides can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, intratumor, or intravenous injection, but even oral, nasal, or anal administration is contemplated. In one embodiment, administration is by subcutaneous or intramuscular injection.

In another embodiment, a pharmaceutical composition includes a nucleic acid encoding the polypeptide or immunogenic fragment thereof. A therapeutically effective amount of the polynucleotide can be administered to a subject in order to generate an immune response. In one specific, non-limiting example a therapeutically effective amount of the polynucleotide is administered to a subject to treat cancer, such as ovarian, colon, prostate, breast, lung, or pancreatic cancer.

One approach to administration of nucleic acids is direct immunization with plasmid DNA, such as with a mammalian expression plasmid. As described above, the nucleotide sequence can encode CSPG4. In one embodiment, the method includes administering to a subject a therapeutically effective amount of a nucleic acid encoding CSPG4 in a pharmacologically acceptable carrier. More than one nucleic acid sequence encoding a polypeptide can be included in the expression vector, so that combinations of polypeptides can be administered.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response) and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a polypeptide can also be expressed by attenuated viral hosts or vectors or bacterial vectors. Recombinant vaccinia virus, adeno-associated virus (AAV), herpesvirus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a polypeptide is introduced directly into cells. For example, the nucleic acid may be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, e.g., U.S. Pat. No. 5,589,466).

The disclosure is illustrated by the following non-limiting Examples.

EXAMPLES

No effective targeted treatment is available for triple negative basal breast cancer (TNBC). Here it is demonstrated that chondroitin sulfate proteoglycan 4 (CSPG4), is predominantly expressed on TNBC cancer tissues and overexpressed on TNBC cells and on breast cancer stem cells (referred to as CSC), identified as $CD44^+$, $CD24^{-/lo}$ cells, in pleural effusions from breast cancer patients and in TNBC cell lines. CSPG4-specific monoclonal antibody (mAb), on its own, significantly inhibited growth and caused regression of established metastasis in an experimental TNBC mouse model and significantly inhibited post-surgery spontaneous lung metastases and tumor recurrence in an orthotopic TNBC mouse model. The human TNBC cell lines used in these two types of tumor models to generate xenograft tumor/metastasis were MDA-MB-435 and MDA-MB-231, both of which display the breast CSC phenotype ($CD44^+$, $CD24^{-/lo}$) in 99% of cells. Mechanistic studies of the targeted therapy revealed that the CSPG4-specific monoclonal antibody (mAb) was able to inhibit both (Phophatidylinositde-3-Kinase) PI3K/PTEN/Akt and Mitogen-activated protein (MAP) kinases (MAPK) pathways signaling. In addition, the CSPG4-specific mAb was capable of reducing tumor angiogenesis. These findings establish CSPG4 as an important therapeutic target for antibody based immunotherapy for reducing post-surgery tumor recurrence and metastasis risk.

Example 1

Materials and Methods

Patients, Pleural Effusions and Cell Preparation.

Pleural effusions from breast cancer patients were obtained under an approved cell and tissue procurement protocol. Briefly, effusions were drained using a PleurX catheter and bottles to collect the fluid. Tumor cells were isolated by ficolling the fluid (typically 500 mL-2 L) to remove debris and red blood cell contamination and cryopreserved. Typical yields of cells were $2 \times 10^8$ to $3 \times 10^{11}$ cells per liter of fluid.

Mice.

Female SCID/BALB/c mice (C.B-Igh-1$^b$IcrTac-Prkdcscid, 6-8 weeks old) were purchased from NCI.

Cell Lines.

The melanoma and the breast cancer cell lines HS578T, MCF-7, MDA-MB-231, MDA-MB-435s, SK-BR-3, SUM149 and T47D were obtained from Duke Comprehensive Cancer Center Cell Culture. All cell lines and human melanoma cell lines M14 and M14/CSPG4 transfectant (additional G418 400 µg/ml) were maintained in RPMI 1640 medium supplemented with 10% FCS, pen-strep-glutamine (Invitrogen).

Antibodies.

The mAb 225.28, 763.74, TP41.2 and TP61.5 which recognize distinct determinants of CSPG4 (Campoli, et al., *Crit. Rev Immunol* 24, 267-296, 2004), the mAb D2.8.5-C4B8 which recognizes a determinant of CSPG4 in formalin fixed and paraffin embedded tissue sections, the anti-idiotypic mAb F3C25 (Perosa, & Ferrone, *Hum Immunol* 23, 255-269, 1988) and MK2-23 and the calnexin-specific mAb TO-5, were developed as described (Kusama et al., *J Immunol* 143, 3844-3852, 1989); Ogino et al., *J Immunol Methods* 278, 33-44, 2003). All mAb are IgG1, except mAb 225.28 and F3C25, which are IgG2a; mAb were purified from ascitis by sequential ammonium sulfate and caprylic acid precipitation (Temponi et al, *Hybridoma* 8, 85-95, 1989). PE-anti-mouse IgG, FITC-CD24, APC-CD44, PerCP-CD45, 7-AAD, and lineage cocktail (CD2, 3, 10, 16, 18, 31, 45, 64, 140b) conjugated antibodies, unconjugated anti-mouse CD31 (PE-CAM1) antibody were purchased from BD/Pharmingen. Specific antibodies were purchased commercially for: PKCα (Sigma); phosphorylated and non-phopho-FAK (BD Bioscience); phosphorylated and pan Akt, phospho-PTEN (Ser380/Thr382/383), phospho-Met (Tyr1234/1235) (D26), phospho-Gab (Tyr 307), phospho-Met (Tyr1003), phospho-p44/42 MAPK (Erk1/2), (Thr202/Tyr204) and phopho-Histone H3(Ser10) (Cell signaling technology).

Gene Expression Analysis.

RMA gene expression data was obtained for a publicly available, clinically annotated breast cancer data set (GEO accession number: GSE5460) consisting of 125 samples and categorized according to hormonal status (ER−/Her2−, ER−/Her2+, ER+/Her2− and ER+/Her2+) (Lu, X., et al., *Breast Cancer Res Treat* 108, 191-201, 2008). Gene expression level corresponding to chondroitin sulfate proteoglycan 4 (CSPG4) (204736_s_at, 214297_at) was obtained for each subgroup and differences between the groups were analyzed via the non-parametric Mann-Whitney U test using Graph Pad Prism Software, version 4.03. A two-sided p-value less than 0.05 was considered statistically significant.

Flow Cytometry Analysis.

Tumor cell preparations from plural effusion were labeled with antibodies to well-characterized surface cell markers (CD44, CD24) to assess the presence and percentage of various cell populations by flow cytometry, looking in particular for CD44$^+$CD24$^{-/low}$ cells, as per Al-Hajj et al. to identify CSC. Briefly, cells were stained with CSPG4-specific mAb for 30 mM, washed twice with PBS, and incubated for 30 min with PE-labeled anti-mouse IgG antibody. After 3 washes, cells were stained with FITC-CD24, APC-CD44 and PerCP-CD45 (CD45 as a lineage marker) or a cocktail of labeled CD2, 3, 10, 16, 18, 31, 45, 64, 140b antibodies and 7AAD (to exclude dead cells) for 30 min. After 2 washes, cells were analyzed by flow cytometry. The same staining procedure applies to breast tumor cell lines, except the use of PerCP-CD45 (CD45 as a lineage marker) or a cocktail of labeled CD2, 3, 10, 16, 18, 31, 45, 64, 140b antibodies.

Immunohistochemistry

CSPG4: Formalin-fixed paraffin-embedded (FFPE) sections of tumors obtained from patients were deparaffinized and hydrated. Antigen retrieval was performed by boiling for 15 mins in 1 mM EDTA (pH 8.0). Slides were blocked by 3% hydrogen peroxidase and 1% bovine serum albumin/5% normal horse serum in Tris-buffered saline with Tween 20 (Sigma-Aldrich Inc., St. Louis, Mo.), and incubated overnight at 4° C. in a closed humid chamber with the CSPG4-specific mAb, D2.8.5-C4B8 (3 µg/ml). Signals were amplified with EnVision+System-HRP (DakoCytomation Inc) and developed by diaminobenzidine (DAB, DakoCytomation Inc.). Samples were counterstained with hematoxylin, dehydrated, and mounted in Canada balsam (Sigma-Aldrich Inc.).

Breast cancer sections stained with CSPG4-specific mAb were graded separately by two investigators utilizing the modified protocol as previously described (Kageshita, T., et al., *Cancer Res* 53, 3349-3354, 1993).

CD31: Zinc (Zinc Fixative, BD Pharmingen) fixed and paraffin embedded tissue sections of surgical removed xenografts were stained with anti-mouse CD31(PECAM1) antibody as previously described (Ko et al., *Cancer Res* 67, 7875-7884, 2007).

Phopos-Histone 3:

FFPE of lung sections were stained with anti-p-Histone3 antibody according to the manufacture's protocol.

Apoptosis:

FFPE of lung sections were stained for apoptotic cells using APOP* Plus Peroxidase In Situ Apoptosis Kit™ (S7101) (Terminal Deoxynucleotidyltransferase-Mediated dUTP Nick End Lebeling (TNUEL) assay) (Millipore) according to the manufacture's protocol.

RT-PCR.

RT-PCR was performed as described (Luo, et al., *Oncogene* 25, 2873-2884, 2006).

Western Blotting.

Western blot assay for CSPG4 was performed as described (Wang, X., et al. *J Immunol Methods* 299, 139-151, 2005); for other signaling related proteins were performed using standard techniques on the following two types of cell lysates: 1) lysate of cultured cells ($2 \times 10^4$ cells/well in a 96-well plate were serum starved for 48 hours, then treated with either mAb 225.28 (0.1 mg/ml), isotype (0.1 mg/ml) or PBS for additional 48 hours), cells were lysed in lysis buffer (10 mM Tris-HC, 1% NP40, 1 mM EDTA, 0.1% BSA, 150 mM NaCl, 1/50 of protease inhibitor cocktail (Calbiochem) and 2) lysate of snap frozen surgically removed xenografts, tissues were homogenized before and after adding an ice-cold RIPA buffer (Thermo Scientific) containing 1/50 of protease inhibitor cocktail (Calbiochem). After vortex 60 seconds, the samples were ice-cooled for 45 min Insoluble material was removed from tissue lysates by centrifugation at 13,000 rpm for 30 mM at 4° C. Protein concentration was measured by Bradford reagent (BioRad).

Cell Growth, Adhesion and Migration.

For cell growth assay, cells ($5 \times 10^4$ cells/well) were serum starved 48 hours and then seeded in a 96-well plate containing 4 times diluted matrigel (growth factor-reduced matrigel-CB-40230, BD Biosciences) and 0.25 mg/ml either mAb 225.28, control mAb F3C25 or PBS in serum free RPMI 1640 medium (total volume 200 μl/well) and cultured in a 37° C. and 5% $CO_2$ incubator for 6 days. Then pictures of cells were taken and cells were trypsinized and counted. For the cell adhesion assay, cells ($2 \times 10^5$ cells/well) were seeded and incubated with 0.05 mg/ml either mAb 225.28, control mAb F3C25 or PBS for 40 minutes in a 96-well plate which was coated with 100 μl/well of 12 μg/ml fibronectin in PBS. Non-adherent cells were washed away with PBS. Adherent cells were fixed by 70% ethanol, stained by crystal violet and resuspended in PBS. Absorbance at 540 nm was measured. The results were expressed as % inhibition of adhesion, utilizing the adhesion values obtained in PBS without mAb as a reference. The values shown were the mean of three independent experiments. For the migration assay, cells ($5 \times 10^4$ cells/well) were serum starved 48 hours and then seeded in a 24-transwell plate (24-well insert, pore size 8 μm; BD Biosciences) with 0.25 mg/ml mAb 225.28, control mAb F3C25 or PBS. The cells migrated toward to serum-free RPMI1640 medium containing 10 μg/ml fibronectin. After 48 hours, migrated cells were stained with HEMA 3 stain set, taken picture and counted under a Zeiss Inverted Fluorescence Microscope (AxioVision Software). Mean of six independent high power field (100×) are shown as columns All of the above experiments were performed in triplicate.

Experimental Lung Metastasis and Treatment Experiments.

SCID mice were intravenously injected with cells MDA-MB-435 or MDA-MB-231 and treated with mAb, as indicated in description of FIG. 4.

Spontaneous Lung Metastasis and Treatment Experiments.

MDA-MB-435 cells were implanted into mammary fat pad of SCID mice. Primary tumors were surgically removed and mAb was administered as indicated in the description of FIG. 5.

Example 2

Preferential CSPG4 Expression in ER Negative and Her2 Negative Breast Cancers

Comparison of the CSPG4 mRNA levels in $ER^-/Her2^-$, $ER^-/Her2^+$, $ER^+/Her2^-$, and $ER^+/Her2^+$ breast cancer cells using a publicly available, clinically annotated breast cancer data set (GSE5460) showed that the CSPG4 gene expression level was significantly (Mann Whitney, p=0.01 to 0.06) higher in the $ER^-/Her2^-$ subgroup than in the other subgroups. It appeared to be best correlated with the basal breast cancer phenotype (ER–/Her2–) (FIG. 1a).

The preferential CSPG4 expression by $ER^-$, $PR^-$ and $Her2^-$ triple negative breast cancer tissues was corroborated by the results of immunohistochemical staining the in different subtypes of human breast cancer using CSPG4-specific mAb. CSPG4 was detected in 72.7% of triple negative breast cancer tissue from 44 patients. In contrast, CSPG4 was detected in 28.6% in $ER^+$ breast cancer tissue from 18 patients and 16.7% of 28 ER+ primary breast cancer lesions an 18 $Her2^+$ breast cancer tissue from 18 patients, respectively (Table 1 and FIG. 1b).

TABLE 1

Differential expression of CSPG4 on tumor subtypes

| $CSPG4^+$ | $ER^+$ | $Her2^+$ | $ER^-PR^-Her2^-$ |
|---|---|---|---|
| (−) | 20/28 (71.4%) | 15/18 (83.3%) | 12/44 (27.3%) |
| (+) | 6/28 (21.4%) | 3/18 (16.7%) | 10/44 (22.7%) |
| (++) | 2/28 (7.2%) | 0/18 (0%) | 18/44 (40.9%) |
| (+++) | 0/28 (0%) | 0/18 (0%) | 4/44 (9.1%) |

Figure 1B:
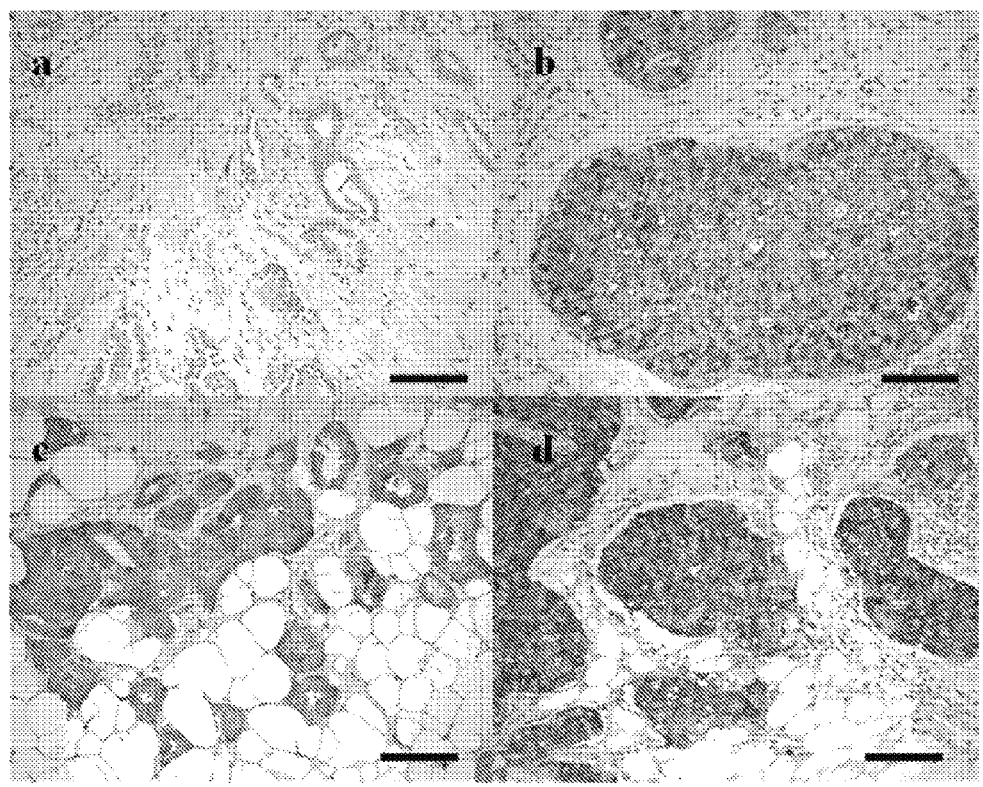

The grading system used is as described in description for FIG. 1b.

Example 3

CSPG4 Expression by a Subpopulation of Breast CSC in TNBC Cell Lines

The frequency of CSC, identified as $CD44^+CD24^{-/lo}$ cells by flow cytometry, is much higher in TMBC than in luminal breast cancer cell lines. They were not detectable in the cell line SK-BR-3, and had a frequency of 1.5 and 34.6% in the cell lines T-47D and MCF-7, respectively. In contrast, they had a frequency of 92.5-99.0% in the TNBC cell lines HS578T, MDA-MB-231, MDA-MB-435 and SUM-149[12] (FIG. 1c). Interestingly, CSPG4 is differentially expressed on $CD44^+$ $CD24^{-/lo}$ cells present in basal and luminal breast cancer cell lines. It has a high expression on a high percentage (66.7-96.1%) of CSC in the 4 TNBC cell lines, but only a low or barely detectable expression on a low percentage (1.5-13.0%) of CSC in the three luminal breast cancer cell lines. (FIG. 1c).

Flow cytometric analysis showed that the distinct determinants recognized by the CSPG4-specific mAb 225.28, 763.74, TP41.2 and TP61.5 are differentially expressed on each cell line, in terms of percentage of stained cells and of staining intensity. In the SUM-149 cell line about 95% of CSC express the determinant recognized by mAb 225.28 and less than 5% those recognized by mAb 763.74 and TP41.2. In contrast, in the MDA-MB-435 cell line at least 90% of CSC express the determinants recognized by the four CSPG4-specific mAbs. The expression patterns of CSPG4 determinants on whole cell populations are comparable to those on autologous CSC in the MDA-MB-435 and SUM-149 cell lines. In contrast, in the MDA-MB-435 cell line about 90% of CSC express the determinants recognized by the four CSPG4-specific mAbs. The expression patterns of the CpSG4 determinants recognized by mAb 763.74 and TP41.2 is lower on CSC than on the autologous whole cell populations in the HS578T and MDA-MB-231 cell lines, suggesting a unique modification of CSPG4 epitopes expressed on CSC (Table 2a, 2b*).

TABLE 2a

Differential expression of distinct CSPG4 determinants
on whole cell population of breast cancer cell lines

| mAb | HS578T %/MFI | MCF-7 %/MFI | MDA-MB-231 %/MFI | MDA-MB-435 %/MFI | SK-BR-3 %/MFI | SUM-149 %/MFI | T-47D %/MFI |
|---|---|---|---|---|---|---|---|
| 225.28 | 66.7/379.2 | 8.5/12.0 | 83.8/53.8 | 96.1/713.6 | 1.5/4.6 | 93.4/193.1 | 13.0/3.8 |
| 763.74 | 61.4/39.2 | 17.4/13.8 | 91.2/154.1 | 93.5/79.2 | 0.0/2.0 | 1.3/2.8 | 0.5/3.4 |
| TP41.2 | 52.6/34.2 | 13.8/11.9 | 88.4/142.3 | 86.8/63.3 | 0.1/2.1 | 0.9/2.8 | 0.3/2.7 |
| TP61.5 | 92.3/109.4 | 3.5/7.8 | 68.3/86.3 | 82.4/61.1 | 0.1/2.4 | 51.1/19.6 | 0.0/2.3 |
| Isotype control | 0.4/13.0 | 0.7/6.2 | 0.3/9.8 | 0.7/9.1 | 1.9/4.3 | 2.0/2.7 | 6.2/10.4 |

TABLE 2b

Differential expression of distinct CSPG4 determinants
on putative CSC in breast cancer cell lines

| mAb | HS578T %/MFI | MCF-7 %/MFI | MDA-MB-231 %/MFI | MDA-MB-435 %/MFI | SK-BR-3 %/MFI | SUM-149 %/MFI | T-47D %/MFI |
|---|---|---|---|---|---|---|---|
| 225.28 | 71.7/195.8 | 11.4/9.8 | 85.7/53.8 | 99.7/694.4 | NA | 95.7/179.0 | NA |
| 763.74 | 33.9/17.6 | 2.6/2.4 | 16.6/6.9 | 96.4/50.5 | NA | 3.0/3.1 | NA |
| TP41.2 | 17.6/14.5 | 2.5/2.5 | 12.0/6.1 | 91.9/40.4 | NA | 1.4/2.7 | NA |
| TP61.5 | 72.4/34.4 | 9.9/3.2 | 75.6/33.6 | 98.0/93.0 | NA | 51.2/10.5 | NA |
| Isotype control | 0.5/10.0 | 0.6/1.8 | 0.4/3.7 | 0.5/3.0 | NA | 0.5/2.5 | NA |

*For the data shown in the tables, the he TNBC cell lines HS578T, MDA-MB-231, MDA-MB-435 and SUM-149 and the luminal cancer cell lines MCF-7, SK-BR-3 and T-47D were stained with the mAb 225.28, 763.74, TP41.2 and TP61.5 which recognize distinct CSPG4 determinants and subjected to FACS analysis. The tables indicate the % of stained cells and the mean fluorescence intensity (MFI) (a) in the whole cell population and (b) in the subpopulation of putative CSC, defined as $CD44^+/CD24^{-/lo}$. $7AAD^+$ cells (dead cells) were excluded through gating in both experiments. NA, not applicable.

The heterogeneity in the expression of CDPG4 determinants is likely to reflect the differences in the glycosylation of this molecule. CSPG4-specific mAb showed only minor variations across multiple cell culture passages. These results indicate that the expression of CSPG4 by a highly tumorigenic subpopulation of breast cancer cells is a stable characteristic.

Example 4

CSPG4 Expression by a Subpopulation of Breast CSC in Pleural Effusions from Patients with Breast Cancer Utilizing the method of Al-Hajj et al. (*Proc Natl Acad Sci USA* 100:3983-3988), 0.71-92.7% of breast CSC were identified as lineage-negative (CD2, 3, 10, 16, 18, 31, 45, 64, 140b), $CD45^-$, $CD44^+$, $CD24^{-/lo}$ in cells isolated from pleural effusions of 14 breast cancer patients (Table 2). Cells with this surface phenotype have been shown to be enriched for highly tumorigenic subpopulations. The percentage of CSC in the lineage-negative pleural effusion cells was low (<10%) in nine patients, intermediate (18.6-35.0%) in four patients and high (92.7%) in one patient. Consistent with the CSC phenotype, the percentage of CSC in whole effusion cells ranged from 0.01% to 0.89% (Table 2). The extent of enrichment differed depending on the CSPG4-specific mAb used for staining, a result consistent with the heterogeneity in the expression of the corresponding determinants observed on cell lines (Table 3).

TABLE 3

Enrichment of putative CSC population in CSPG4 positive cells
in pleural effusions from patients with breast carcinoma*

| Patient sample # | $CD44^+CD24^{-/lo}$ cells in $CD45^-$ cells (%) | % of $CD44^+CD24^{-/lo}$ in $CSPG4^+$ cells (fold enrichment) | | | | | Highest % and fold enrichment |
|---|---|---|---|---|---|---|---|
| | | mAb 225.28 | mAb 763.74 | mAb TP41.2 | mAb TP61.5 | Average | |
| PC-P4 | 2.91 | 8.6 (2.96) | 5.7 (1.96) | 10.2 (3.51) | 24.7 (8.49) | 12.3 (4.23) | 24.7 (8.49) |
| PC-P5 | 16.3 | 26.8 (1.64) | 68.9 (4.23) | 23.7 (1.45) | 18.3 (1.12) | 34.4 (2.11) | 68.9 (4.23) |
| PC-P6 | 7.21 | 4.7 (0.65) | 0.0 (0.00) | 3.57 (0.50) | 50.0 (6.93) | 14.6 (2.02) | 50.0 (6.93) |
| PC-P7 | 19.2 | 35.5 (1.85) | 95.4 (4.97) | 61.3 (3.19) | 75.4 (3.93) | 66.9 (3.48) | 95.4 (4.97) |
| PC-P8 | 18.0 | 2.9 (0.16) | 60.7 (3.37) | 20.9 (1.16) | 31.3 (1.74) | 29.0 (1.61) | 60.7 (3.37) |
| PC-P9 | 3.38 | 22.6 (6.69) | 40.2 (11.9) | 38.5 (11.4) | 35.7 (10.6) | 34.3 (10.1) | 40.2 (11.9) |
| PC-P10 | 31.6 | 91.5 (2.90) | 96.8 (3.06) | 93.7 (2.97) | 94.8 (3.00) | 94.2 (2.98) | 96.8 (3.06) |
| PC-P11 | 13.0 | 67.4 (5.18) | 93.3 (7.18) | 70.3 (5.41) | 75.5 (5.81) | 76.6 (5.89) | 93.3 (7.18) |
| PC-P12 | 4.94 | 13.5 (2.73) | 96.2 (19.5) | 90.3 (18.3) | 67.3 (13.6) | 66.8 (13.5) | 96.2 (19.5) |
| PC-P13 | 11.6 | 71.0 (6.12) | 81.4 (7.02) | 68.7 (5.92) | 76.7 (6.61) | 74.5 (6.42) | 81.4 (7.02) |

TABLE 3-continued

Enrichment of putative CSC population in CSPG4 positive cells in pleural effusions from patients with breast carcinoma*

| Patient sample # | CD44+CD24−/lo cells in CD45− cells (%) | % of CD44+CD24−/lo in CSPG4+ cells (fold enrichment) | | | | | Highest % and fold enrichment |
|---|---|---|---|---|---|---|---|
| | | mAb 225.28 | mAb 763.74 | mAb TP41.2 | mAb TP61.5 | Average | |
| PC-P14 | 12.2 | 8.4 (0.69) | 91.5 (7.50) | 49.1 (4.02) | 32.0 (2.62) | 45.3 (3.71) | 91.5 (7.50) |
| PC-P15 | 58.7 | 69.3 (1.18) | 90.3 (1.54) | ND | ND | 79.8 (1.36) | 90.3 (1.54) |
| Average (fold enrichment) | 16.59 | 35.2 (2.73) | 68.4 (6.02) | 48.2 (5.25) | 52.9 (5.86) | 52.4 (4.78) | 74.1 (7.14) |

*Tumor cells from pleural effusions from 12 patients with metastatic breast cancer were sequentially incubated with CSPG4-specific mAb 225.28, 763.74, TP41.2, or TP61.5, with PE-labeled anti-mouse IgG antibodies and with FITC-labeled anti-CD24, APC-labeled anti-CD44, PerCP-labeled anti-CD45, and 7-AAD. Stained cells were subjected to FACS analysis. The percentages of CD44+CD24−/lo cells in the CD45− 7-AAD− population and in the CD45− 7-AAD− CSPG4+ population were determined. Enrichment of CD44+CD24−/lo population by gating at CSPG4 positive cells was calculated by dividing the percentage of CD44+CD24−/lo cells in the CD45− 7-AAD− CSPG4+ population by that in the CD45− 7-AAD− population and is shown in parenthesis in each well. The highest percentages and fold enrichment are shown in the right column for each patient's sample.

TABLE 4

Percentage of putative CSC in pleural effusions from patients with breast carcinoma

| Patient sample # | Total cell number (×10^6) | CD44+CD24−/lo cells in CD45−Lin− cells (%) | CD44+CD24−/lo cells in total cells (%) | CD44+CD24−/lo cell number (×10^3) |
|---|---|---|---|---|
| PC-P1 | 34 | 0.71 | <0.01 | 0.8 |
| PC-P2 | 40 | 18.60 | 0.01 | 4.0 |
| PC-P3 | 6 | 8.57 | 0.08 | 4.8 |
| PC-P4 | 280 | 1.61 | 0.01 | 28.0 |
| PC-P5 | 4170 | 2.53 | 0.34 | 14178.0 |
| PC-P6 | 298 | 35.00 | 0.89 | 2652.2 |
| PC-P7 | 220 | 28.90 | 0.01 | 22.0 |
| PC-P8 | 360 | 23.10 | 0.01 | 36.0 |
| PC-P9 | 98 | 1.56 | <0.01 | 9.6 |
| PC-P10 | 1300 | 7.14 | <0.01 | 4.5 |
| PC-P11 | 200 | 4.01 | 0.01 | 20.0 |
| PC-P12 | 1000 | 1.64 | <0.01 | 1.6 |
| PC-P13 | 2515 | 0.99 | <0.01 | 12.4 |
| PC-P15 | 58 | 92.70 | 0.07 | 40.6 |

Example 5

Molecular Profile of CSPG4 Expressed by Breast CSC

CSPG4 mRNA was detected by RT-PCR in MDA-MB-435 cells, most (99%) of which express the CSC phenotype (CD44+CD24−/lo) (FIG. 6a). Western blot analysis with mAb 763.74 of a MDA-MB-435 cell lysate detected the two components of CSPG4 (FIG. 6b).

Example 6

Figure 2A:
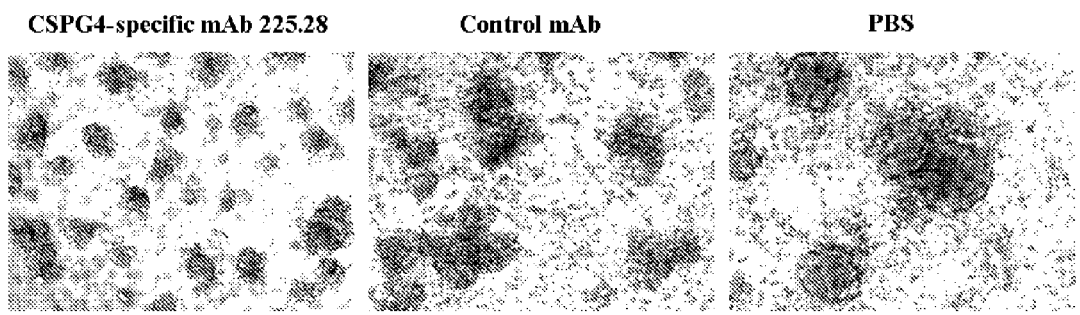
FIGS. 2A-2D are digital images and graphs showing the effects of CSGG4-specific monoclonal antibodies on TNBC cells.
Figure 2B:
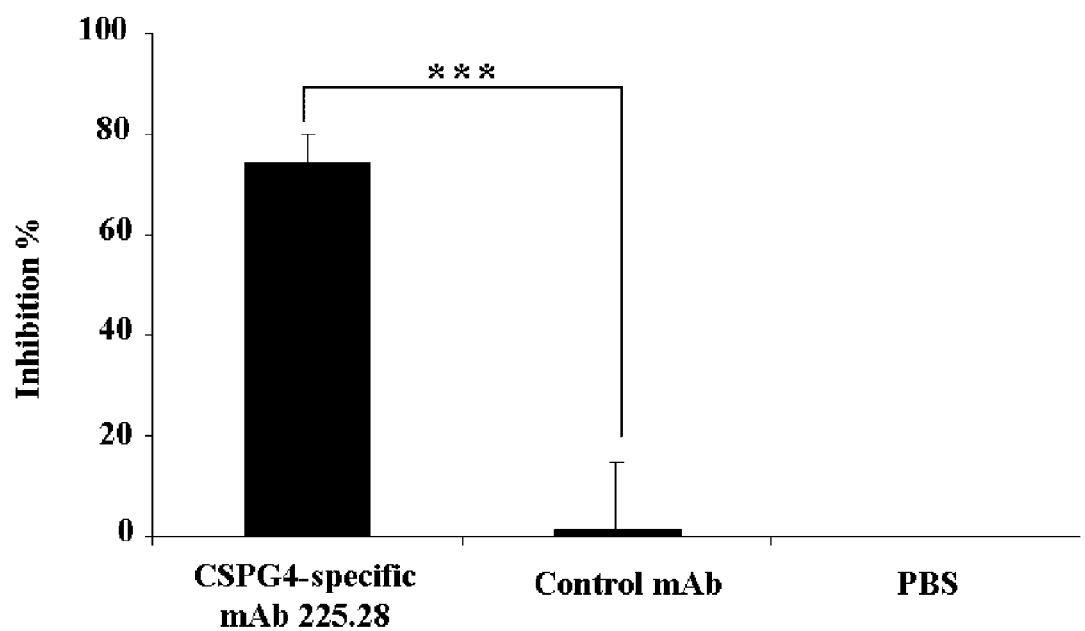
Figure 2C:
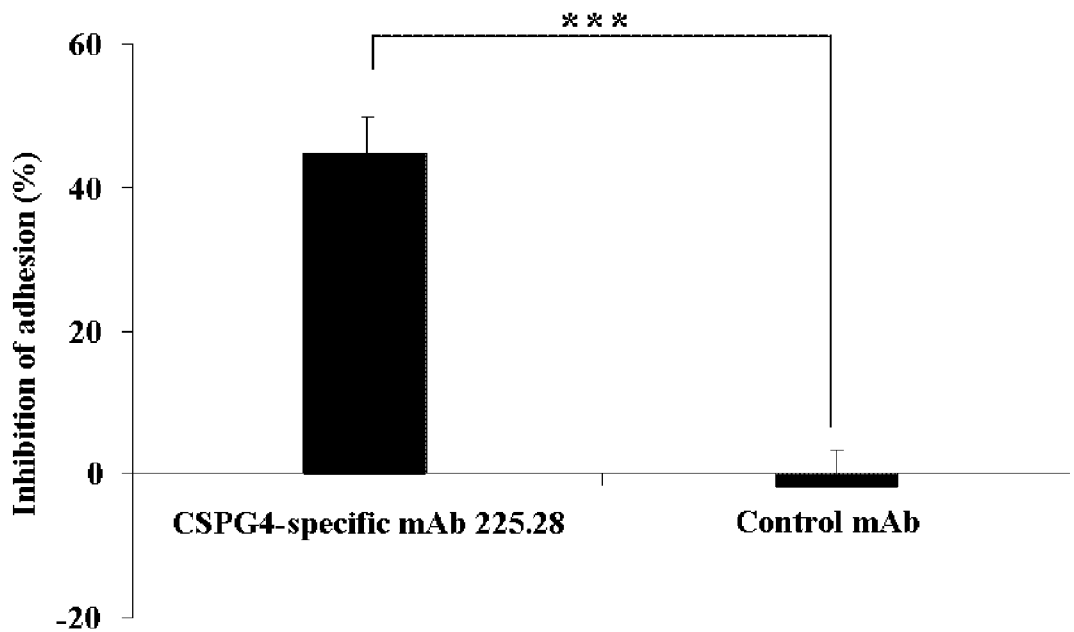
Figure 2D:
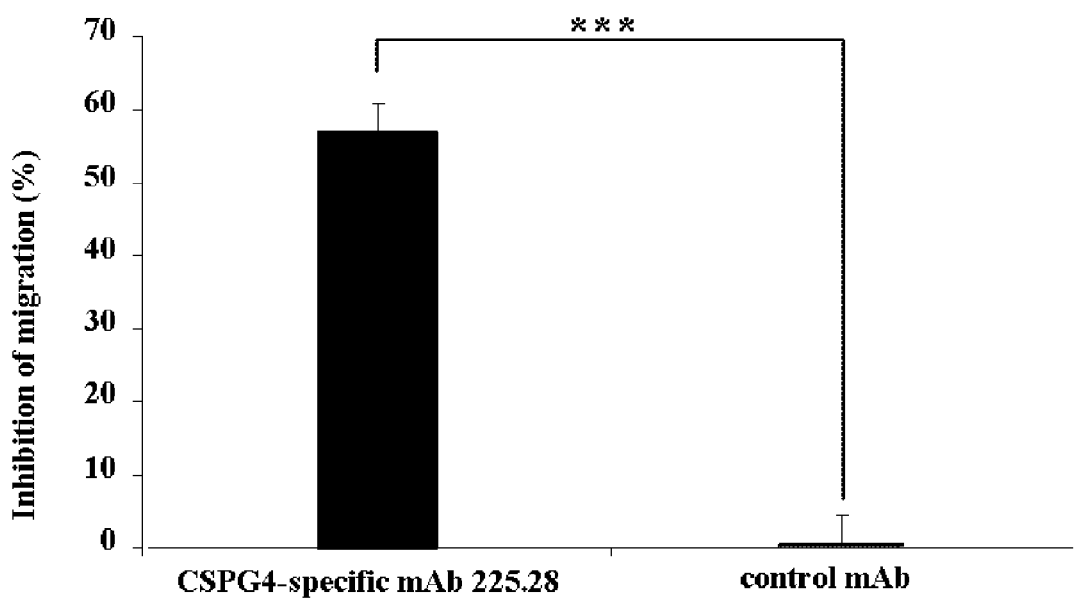

Inhibition by CSPG4-Specific mAb of Tumor Cell Growth, Adhesion and Migration In Vitro via Inhibiting PI3K/PTEN/Akt and MARPK Pathways Signaling Previous work had shown that CSPG4 promotes progenitor and tumor cell motility, adhesion and growth resulting in melanoma and glioma cell growth and metastasis. The CSPG-specific monoclonal antibodies were tested for their ability to block tumor cell motility and growth in vitro. As shown in FIG. 2, CSPG4 specific mAb 225.28 inhibited cell growth, adhesion and migration in CSPG4+ TNBC cells in vitro. As shown in FIG. 2, TNBC cells in the presence of mAb 225.28 at indicated dosages exhibited 70% inhibition (FIG. 2a,b) of cell growth in a 3D matrix setting, which resembles closely to in vivo tumor growth conditions; the adhesion of these cells to fibronectin was also inhibited by 45% (FIG. 2c) and the motility of these cells towards fibronectin in a Boyden chamber assay was inhibited by 56% (FIG. 2d).

Figure 3:
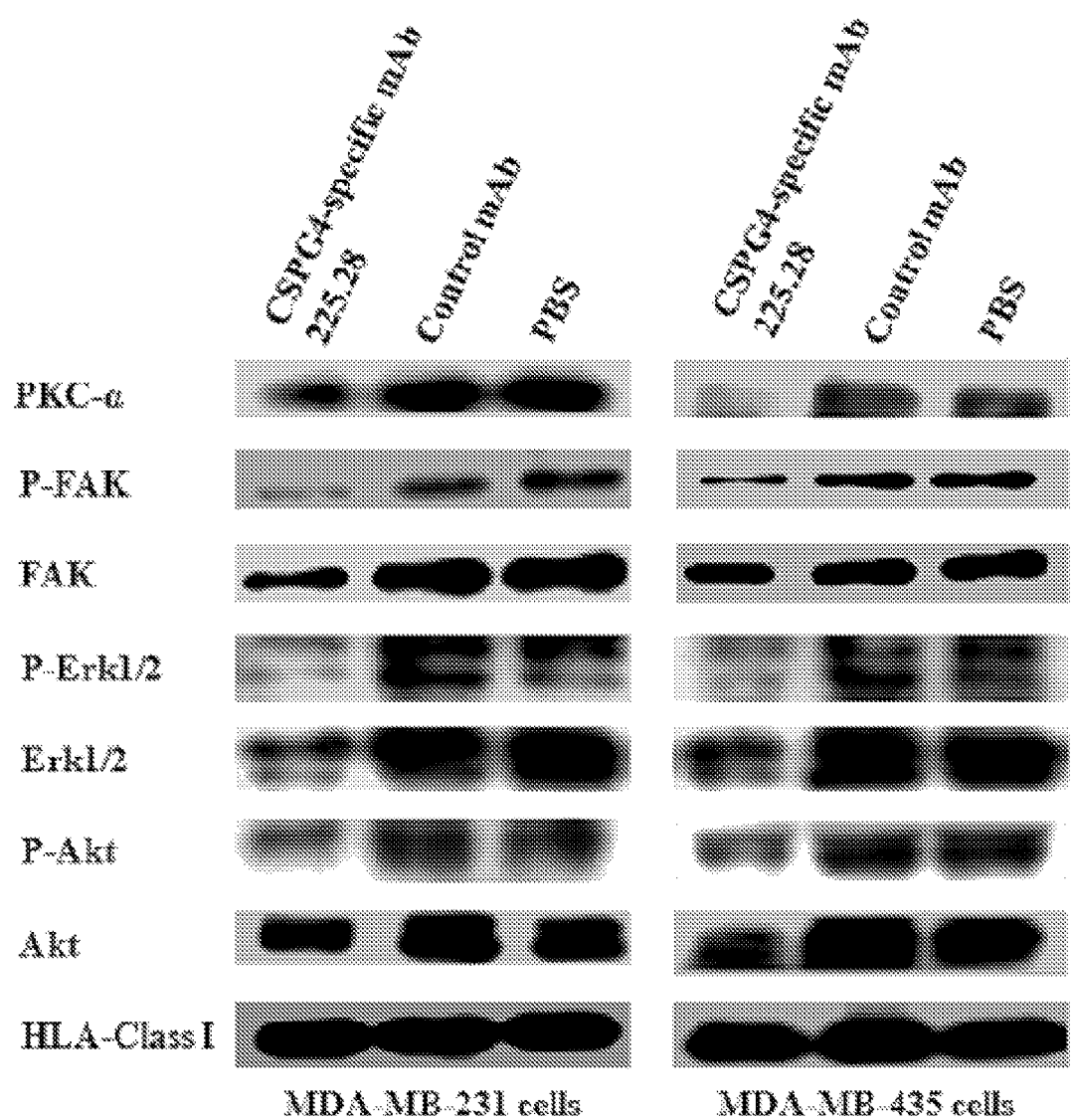
FIG. 3 is a digital image showing the down regulation of signaling relevant to cell growth, adhesion and migration by CSPG4-specific mAb 225.28. Western blotting of PKC-α, p-FAK, FAK, p-Erk1/2, Erk1/2, p-Akt and Akt in indicated cultured cells treated with either mAb 225.28, isotype mAb F3C25 or PBS. HLA class I antigens were used as loading controls.

Previous studies had shown that CSPG4 functions to modify multiple signal transduction pathways that impact on the cytoskeleton, growth, motility and survival of tumor cells. Specifically, several key pathways have been identified as related to the function of CSPG4. These pathways include protein kinase C(PKC) α, FAK, Erk 1, 2 and PI3 kinase, which are all activated and associated with triple negative breast cancer. As shown in FIG. 3, mAb 225.28 in vitro incubation with the CSPG4-specific monoclonal antibody 225.28 inhibited the expression of PKCα and well as the activation of FAK, Erk 1, 2 and AKT in both MDA-MB-231 and MDA-MB-435 cells.

Example 7

Figure 4A:
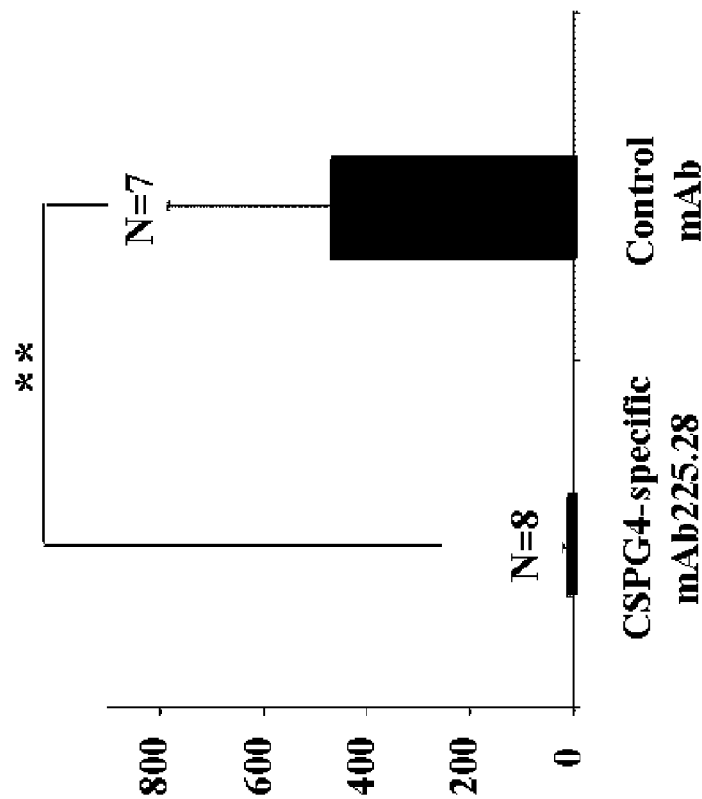
FIGS. 4A-4E are graphs and digital images showing the effects of CSPG4-specific mAb in vivo.
Figure 4B:
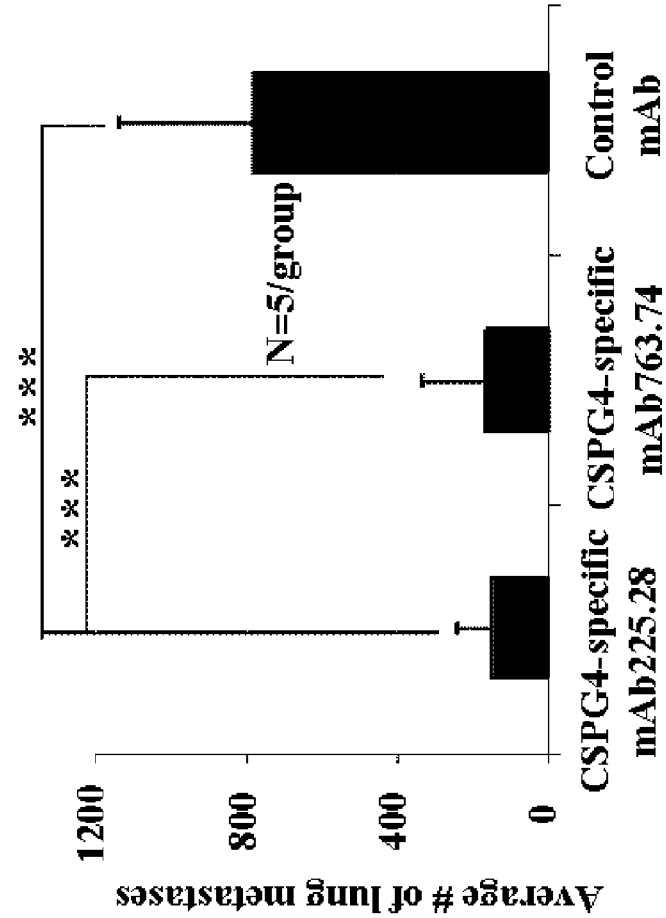
Figure 4C:
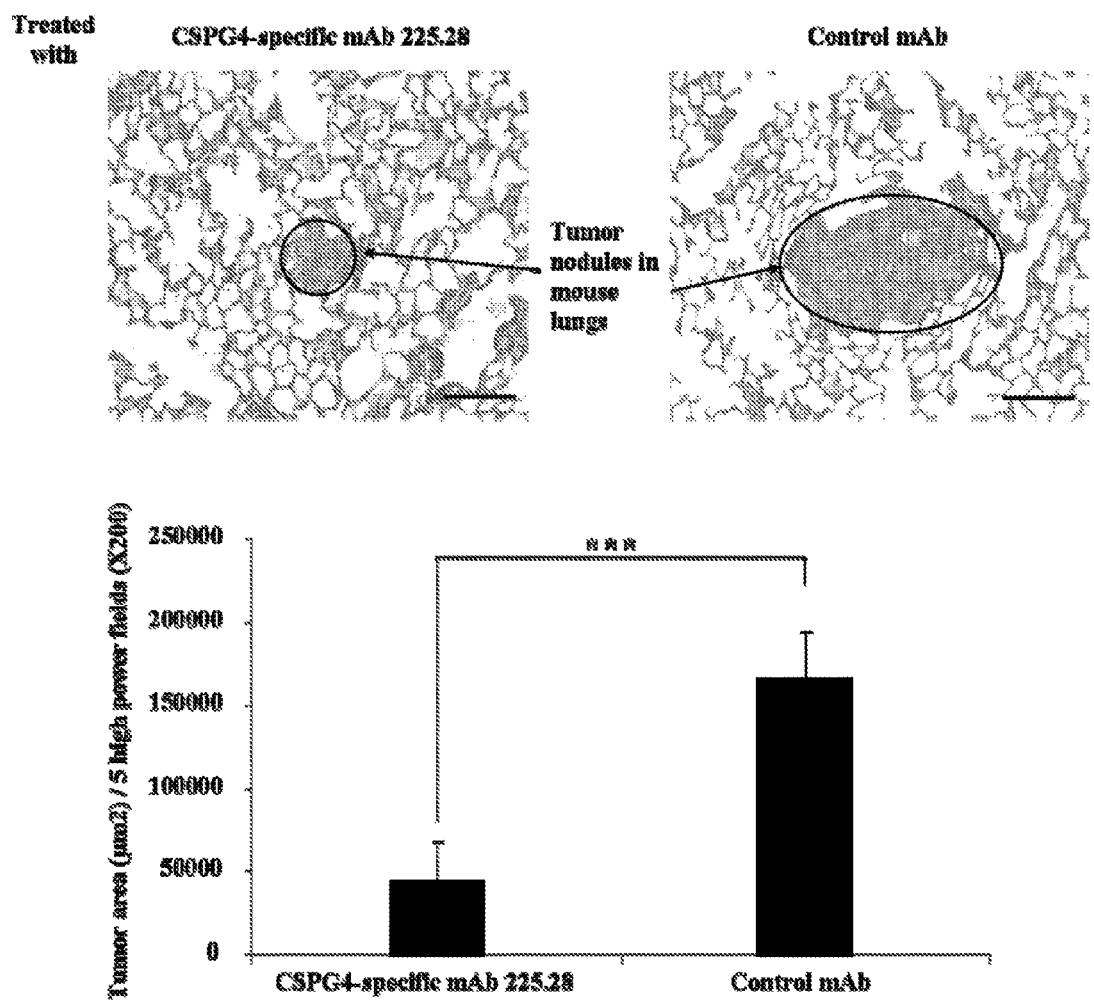
Figure 4D:
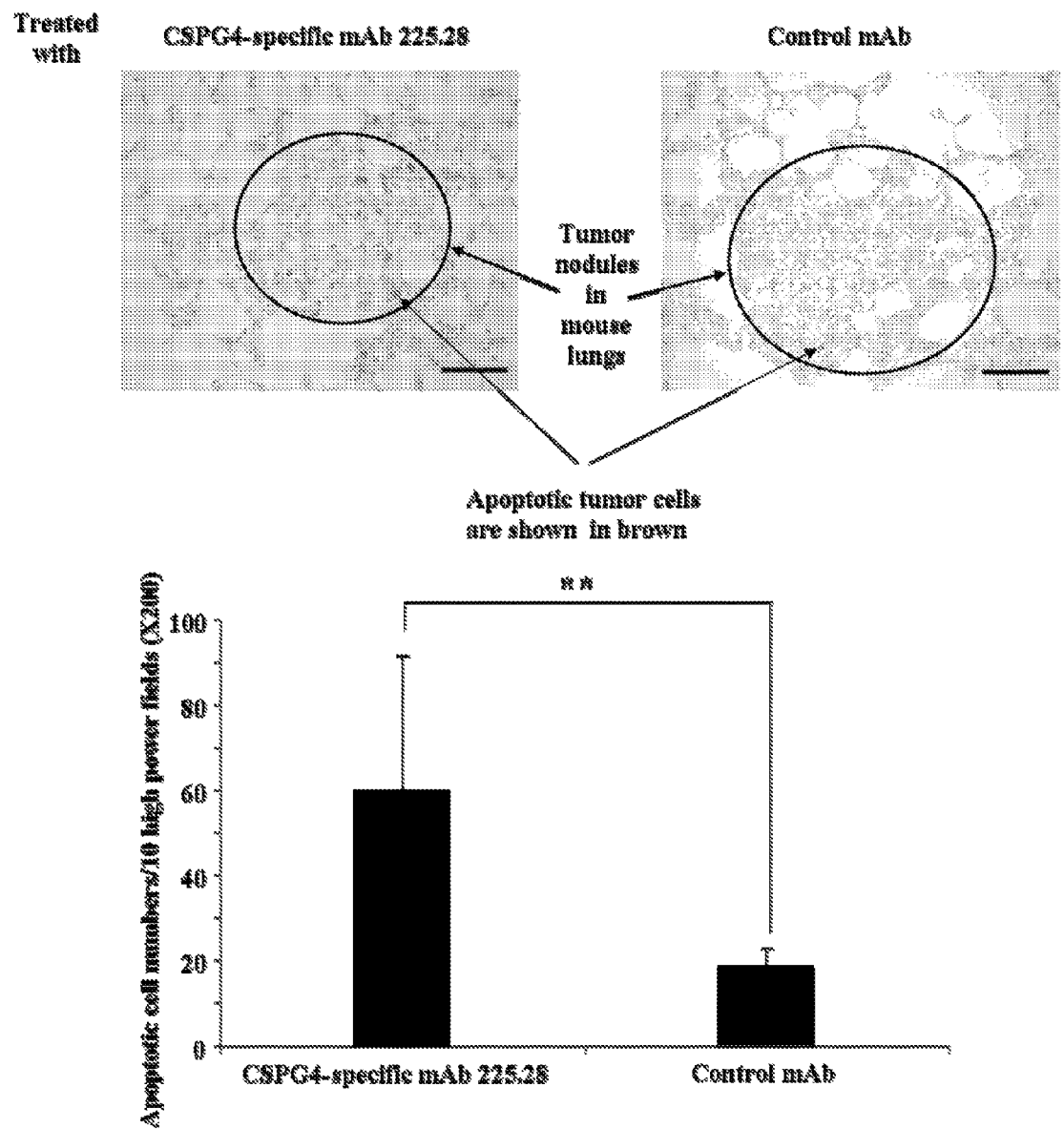
Figure 4E:
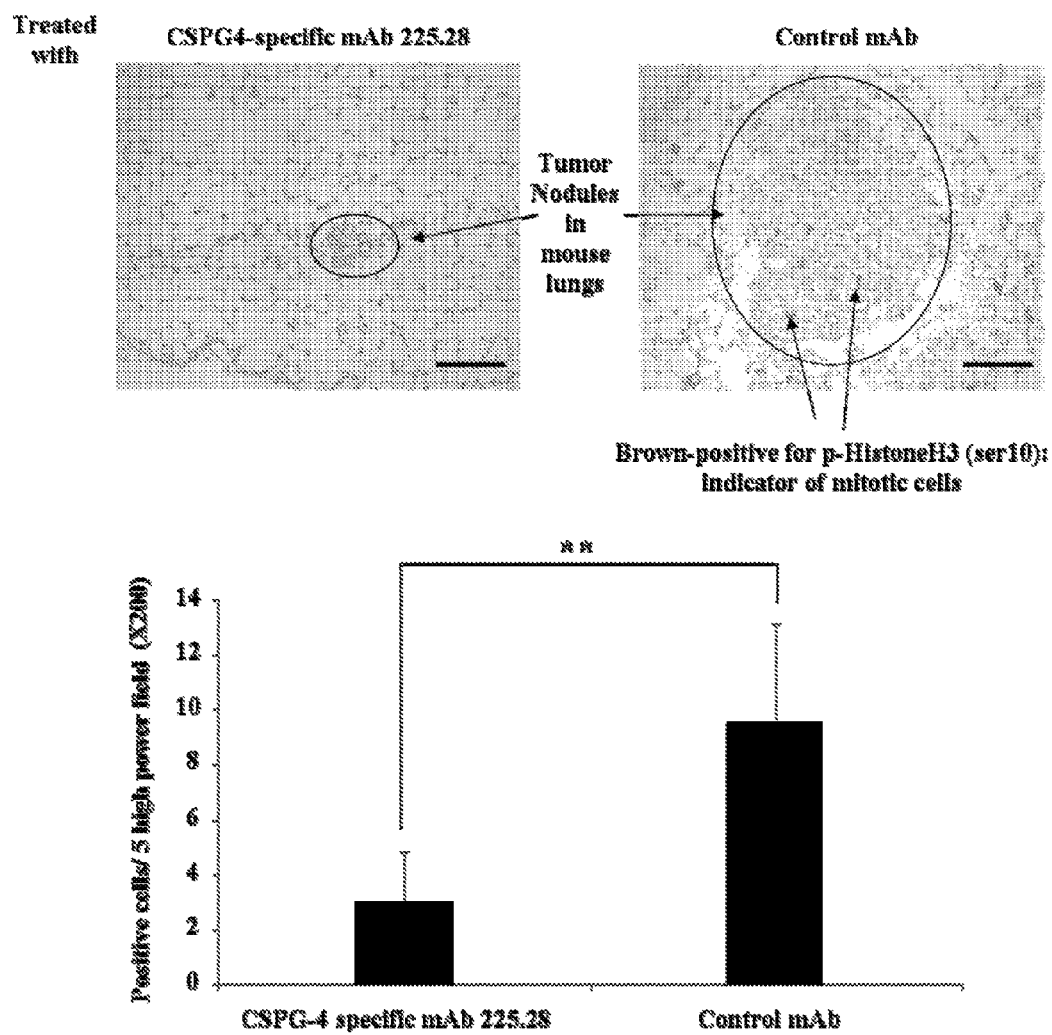

Inhibition/Regression by CSPG4-Specific mAb of Human TNBC Established Experimental Metastasis In Vivo The CSPG4-specific mAb 225.28 inhibited experimental metastases of MDA-MB-231 cells, which have a high percentage of CD441CD24−/lo. cells and a medium to high level of CSPG4 expression (FIG. 4A). On day 3 following an intravenous (i.v.) injection of tumor cells, mice were divided randomly into two groups: one group was injected twice weekly with mAb 225.28 (100 μg/injection) and the other one with a control mAb (100 μg/injection). Evaluation of mice 79 days post tumor cell inoculation demonstrated that CSPG4-specific mAb inhibited MDA-MB-231 metastasis by greater than 99% compared to the control mAb. Similarly, metastasis of MDA-MB-435 cells, which have a high CSPG4 expression, and a CD44+/CD24−/lo phenotype similar to that of MDA-MB-231 cells, was inhibited by greater than 95% with either mAb 225.28 or mAb 763.74 compared to control mAb (FIG. 4b).

Example 8

Figure 5A:
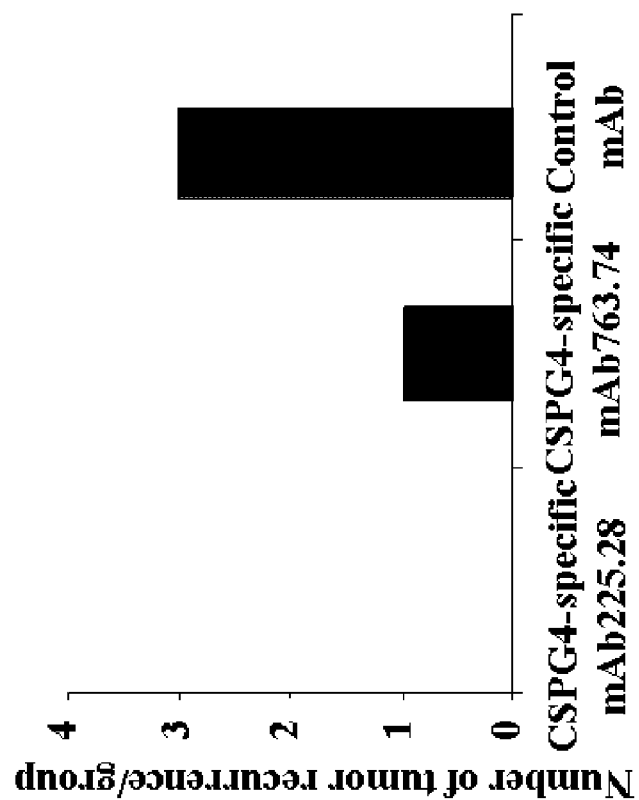
FIGS. 5A-5D show the effect of CSPG4-specific mAb in vivo.
Figure 5B:
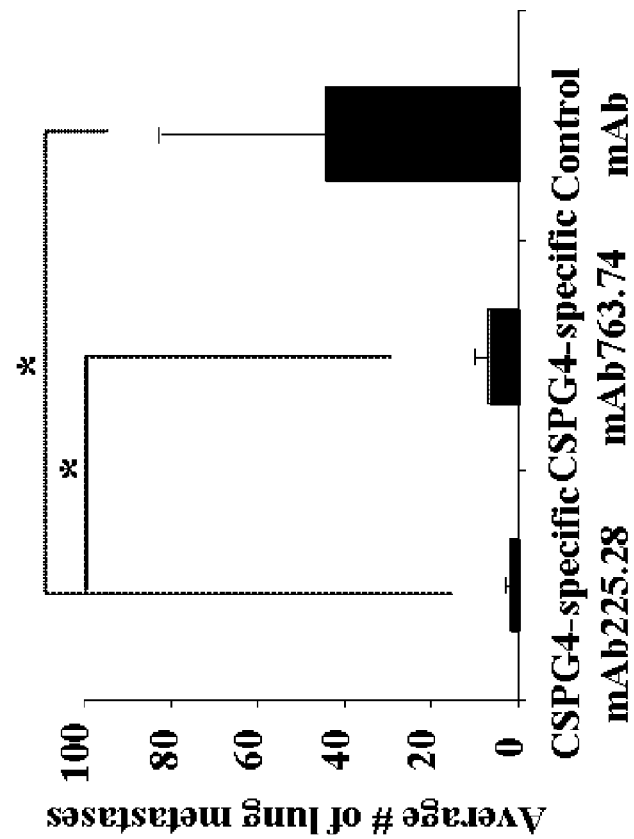

Inhibition by CSPG4-Specific mAb of Human Orthotopic TNBC Tumor Post-Surgery Recurrence and Spontaneous Metastasis In Vivo via Inhibiting PI3K/PTEN/Akt and MARPK Pathways Signaling To conduct a study which is clinical relevant, the ability of CSPG4-specific mAb to inhibit tumor recurrence and spontaneous metastasis of human breast MDA-MB-435 mammary tumors in SCID mice was examined following surgical removal of primary tumors, a setting which resembles the human disease clinically. Mice treated with mAb 225.28 and 763.74 had significantly lower spontaneous lung metastases (FIG. 5a) than those administered with the control mAb. In addition, only one small size local tumor recurrence and no recurrences were detected in the two groups of 5 mice each, treated with mAb 763.74 and 225.28, respectively. In contrast, three large size tumor recurrences were found in the five mice treated with the control mAb (FIG. 5B). The results are representative of two independent experiments. The results indicate that targeting CSPG4 can be useful clinically to inhibit both tumor metastasis and recurrence after primary tumor surgical removal.

Figure 5C:
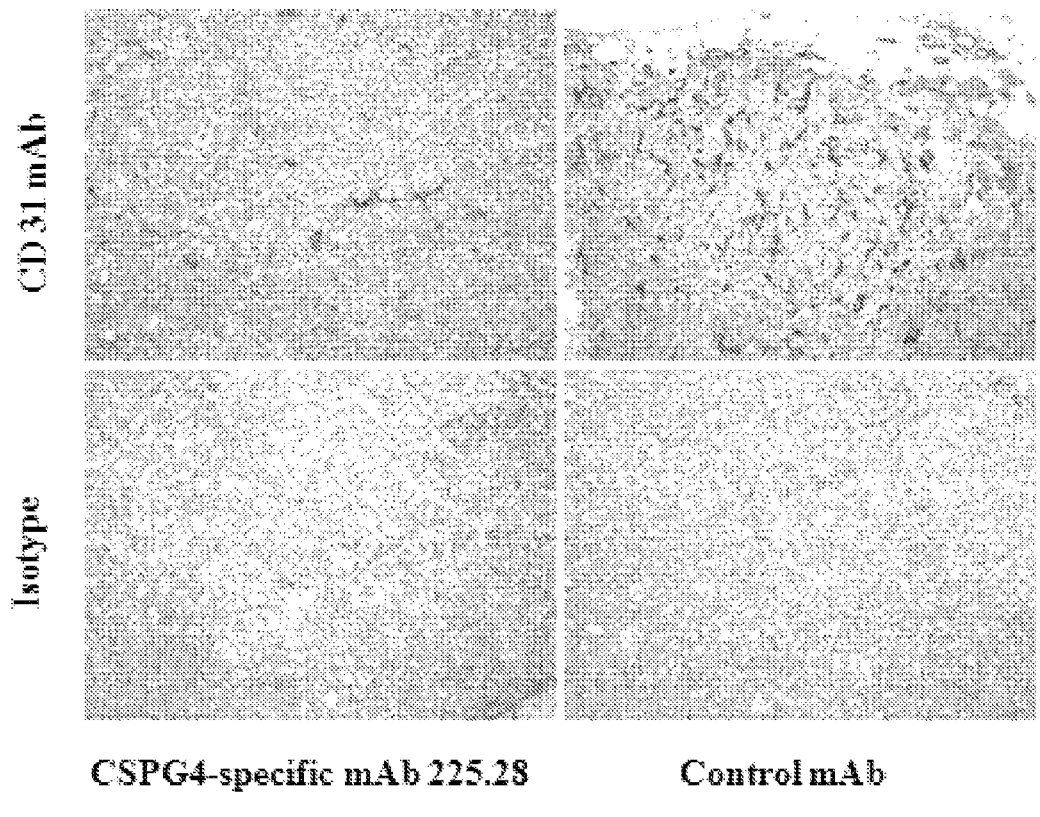
Figure 5D:
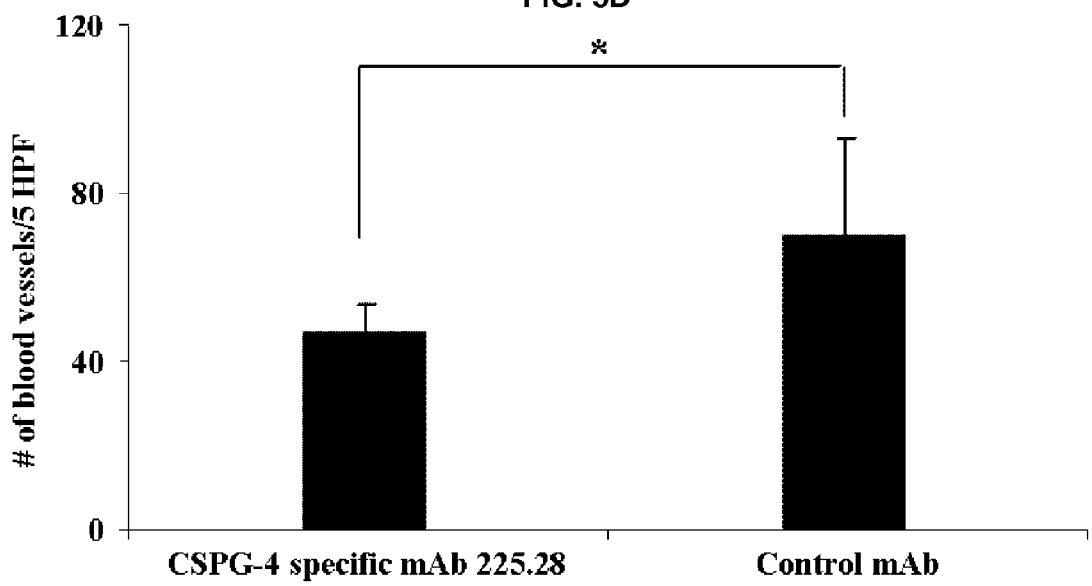

Primary tumors surgically removed from mice treated with mAb 225.28 exhibited a significantly lower level of vascular density compared to primary tumors from mice treated with a control mAb (FIGS. 5C and 5D). The effect on vascular density may be due in part to the targeting of pericytes which express CSPG4 and are important for the maturation of newly forming vessels within tumors.

Figure 5E:
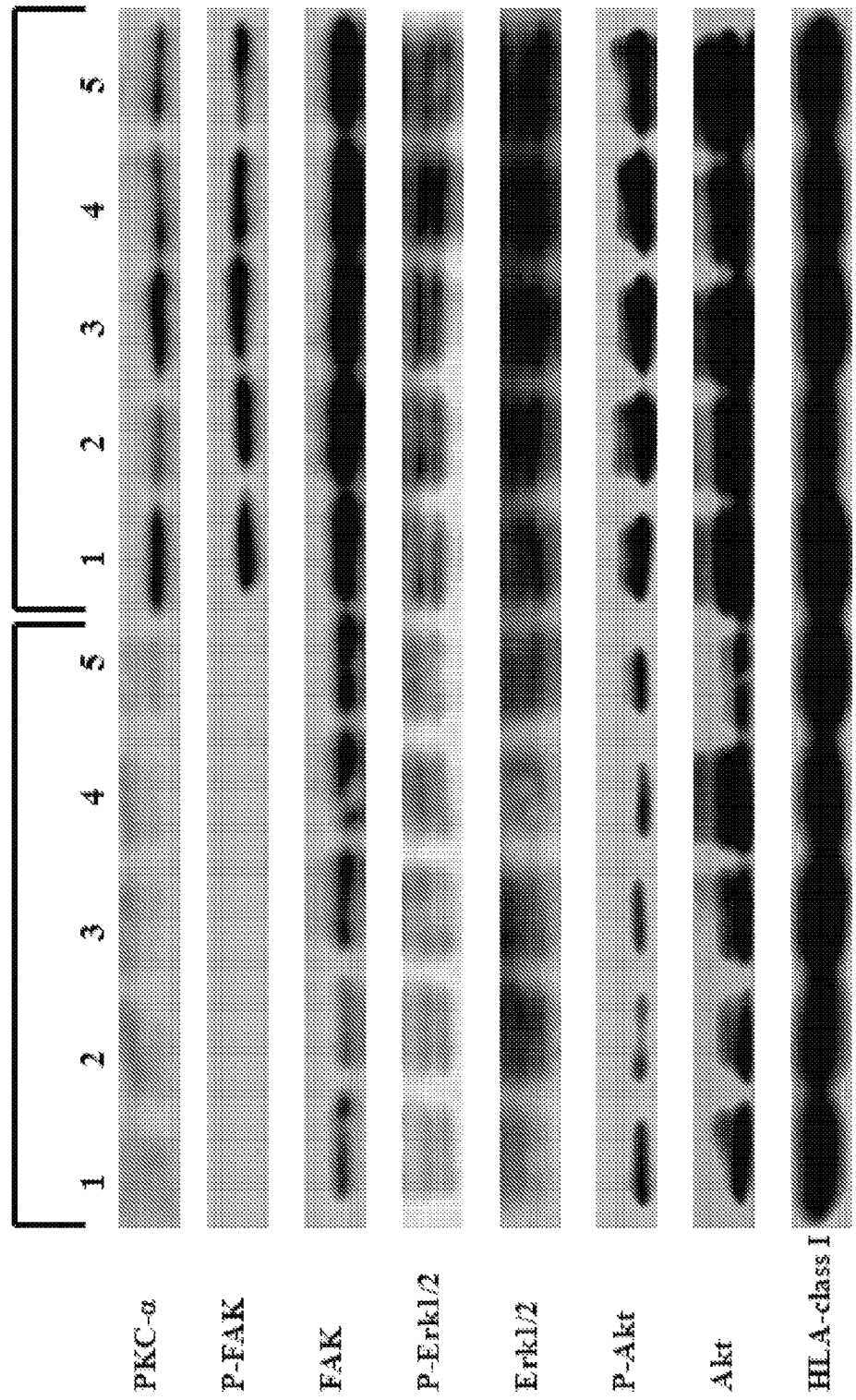

Cell lysates generated from primary tumors removed from mice treated with the CSPG4-specific mAb 225.28 and from mice treated with a control mAb were also evaluated for the activation of specific signal transduction pathways associated with TNBC growth and progression. They include the integrin mediated signaling, as shown by FAK activation and the key tumor cell-growth promoting and -survival signaling pathways, as shown by activation of Erk 1,2 and Akt, respectively. The activation of these three signaling pathways was markedly reduced in the primary tumors removed from the mice treated with the CSPG4-specific mAb 225.28 as compared to those removed from the mice treated with a control mAb. Furthermore, primary tumors removed from the mice treated with CSPG4-specific mAb also exhibited lower levels of PKCα compared to those from the mice treated with a control mAb (FIG. 5E). These results show that targeting CSPG4 with mAb has significant inhibitory effects on the cell growth, adhesion and survival related pathways important for breast cancer progression and metastasis.

Gene-expression profiling, immunochemical studies and immunohistochemical staining have convincingly shown that in breast cancer CSPG4 is preferentially expressed in basal/TNBC. The differential expression of CSPG4 in basal and luminal breast cancer both in differentiated cells and in cells with the CSC phenotype is not unique to CSPG4, since an association between EGFR expression and the basal-like phenotype has also been demonstrated (Korshing et al., *Lab Invest* 82:1525-1533, 2002). Furthermore, IHC staining has detected cytokeratins CK5/6, S-phase kinase-associated protein 2 (SKP2) and mesenchyme forkhead 1 (FOXC2) mainly in basal/TNBC lesions (Mani et al., *Proc Natl Acad Sci USA* 104:10069-10074, 2007). Whether the differential CSPG4 expression in TNBC and other breast cancer subtypes reflects the different cell types from which they originate, or differences in the mechanism(s) of regulating gene expression in different subtypes of breast cancer remains to be determined. On the other hand the lack or low level of CSPG4 expression in other subtypes of breast cancer is not likely to reflect loss of the encoding genes, since loss of genetic material in chromosome 15 where CSGP4 has been mapped (28) has not been described in these subtypes of breast cancer. Whatever the molecular mechanism(s) underlying CSPG4 gene activation in TNBC is (are), its preferential expression in this breast cancer subtype suggests its potential use as a diagnostic biomarker and as a therapeutic target.

In TNBC, CSPG4 appears to be expressed mostly, although not exclusively on subpopulations with the $CD44^+CD24^{-/lo}$. phenotype. This cell subpopulation, which is enriched in this subtype of breast cancer, appears to play a major role in progression, since cells with a $CD44^+CD24^{-/lo}$. phenotype have a high invasive potential that facilitates metastasis to lung (Sheridan, *Breast Cancer Res* 8:R59, 2006) and represent the majority of cancer cells detected in the bone marrow of breast cancer patients (Balic et al., *Clin Cancer Res* 12:5615-5621, 2006). Given the role of CSPG4 in migration, metastasis (Burg et al, *J Cell Physiol* 177:299-312, 1998) and chemo-resistance (Checkenya, *Oncogene* 27:5182-5194, 2008) of malignant cells, as well as its expression on pericytes (Ozerdem, *Angiogenesis* 7:269-276, 2004), which may be the origin of mesenchymal cells (Crisen, *Cell Stem Cell* 3:301-313, 2008), it is possible that that the core protein of this cell surface proteoglycan contributes to the stem-like properties of this subpopulation and to their epithelial-mesenchymal transition (EMT). The latter morphologic transdifferentiation process enables carcinoma cells to acquire a mesenchymal appearance/gene expression profile which contributes to increased motility and invasiveness during malignant progression (Hay, *Acta Anat (Basel)* 154:8-20, 1995).

CSPG4-specific mAb are effective at inhibiting the metastasis of multiple TNBC cell lines, including MDA-MB-231 and MDA-MB-435 cells. The MDA-MB-435 cell line is tested in these studies as a model for evaluating the tumor metastasis and recurrence of $CSPG4^+CD44^+CD24^{-/lo}$ cells and for establishing proof of principle for the efficacy of targeting CSPG4 with mAb in cells with aggressive metastatic phenotype in a preclinical model.

Basal/TNBC are associated particularly with aggressive behavior and poor prognosis, and typically do not express hormone receptors or HER-2 (the "triple-negative" phenotype). Therefore, TNBC patients are unlikely to benefit from currently available targeted systemic therapy. Moreover, EGFR targeted therapy by cetuximab in metastatic basal/TNBC yielded rather disappointing results in clinical trials. To overcome this limitation, proteins predominantly expressed on basal/TNBC, such as CSPG4, are attractive candidates for therapeutic targets. The function-blocking CSPG4-specific mAb 225.28, inhibits in vitro tumor cell growth, adhesion and migration and in vivo tumor cell proliferation and tumor angiogenesis and induce tumor cell apoptosis within the primary tumor consisting of TNBC cells. As a result, CSPG4-specific mAb caused >70% regression of established TNBC cell derived lung metastases and inhibited recurrences and metastatic spreading following the surgical removal of primary tumors.

Basal/TNBC are associated particularly with aggressive behavior and poor prognosis, and typically do not express hormone receptors or HER-2 (the "triple-negative" phenotype). Therefore, TNBC patients are unlikely to benefit from currently available targeted systemic therapy. Moreover, EGFR targeted therapy by cetuximab in metastatic basal/TNBC has yielded rather disappointing results in clinical trials within the primary tumor consisting of TNBC cells. As a result, CSPG4-specific mAb causes >70% regression of established TNBC cell derived lung metastases and inhibits recurrence and metastasis of primary tumors that have been removed surgically. CSPG4-specific mAb also inhibit the activation of signal transduction pathways important for the malignant progression of TNBC cells.

Previous studies have demonstrated that CSPG4 and the NG2 rat homologue are associated with several of these key pathways in other tumor models. These include those important for cytoskeletal reorganization (e.g. cdc42 and Rac), integrin mediated adhesion (e.g. FAK activation), growth promoting pathways (e.g. sustained Erk 1,2 activation) and cell survival pathways (e.g. Akt activation). Targeting CSPG4 with mAb has a pleiotropic effect on the TNBC cells. This is in contrast to other current therapeutic mAb such as herceptin, which appear to target PI3K/Akt related pathways without inhibiting growth related signaling pathways such as the sustained activation of Erk 1,2. The CSPG4-specific mAb 225.28 did not appear to exhibit antibody-dependent, cell-mediated cytotoxicity as in vivo depletion of NK cells in SCID mice had no impact on its therapeutic efficacy. Furthermore, the antibody did not mediate complement-dependent cytotoxicity of tumor cells. Collectively, these data indicate that the inhibitory effect of mAb 225.28 on tumor growth and metastasis is a direct result of its ability to inhibit signaling pathways important for the malignant progression of tumor cells.

There are significant efforts to target certain proteins, such as SHh and wnt related signaling pathways that are associated with a 'stem cell like' tumor phenotype. CSPG4 has restricted distribution in normal tissues and is associated with progenitor populations within different organs. However, it offers advantages as a therapeutic target over other targets as the SHh and Wnt signaling pathways, since CSPG is not fundamentally required for normal stem cell maintenance and self renewal. Consequently, targeting of CSPG4 with mAb is unlikely to be associated with the negative effects on normal tissue stem cells. CSPG4-specific immunity does not appear to cause side effects in humans and did not cause general toxicity, such as body weight loss and delay in wound healing in mice after a half year systemic administration (twice weekly) of mAb 225.28. The exquisite specificity of CSPG4-specific mAb makes these antibodies ideally suited for targeting highly tumorigenic/metastatic cell subpopulations within malignant tumors. It is disclosed herein that the exquisite specificity of monoclonal antibodies may be ideally suited to treatment of cancer stem cells bearing high levels of CSPG4 expression.

It will be apparent that the precise details of the methods or compositions described may be varied or modified without departing from the spirit of the described invention. We claim all such modifications and variations that fall within the scope and spirit of the claims below.

The invention claimed is:

1. A method for inhibiting the growth of a triple negative basal breast cancer cell in a subject, comprising:
   selecting a subject that has triple negative basal breast cancer; and
   contacting the triple negative basal breast cancer cell with an effective amount of an antibody that specifically binds chondroitin sulfate proteoglycan 4 (CSPG4), thereby inhibiting the growth of the triple negative cancer cell.

2. The method of claim 1, wherein the antibody is covalently linked to an effector molecule.

3. The method of claim 1, wherein the antibody is a monoclonal antibody.

4. The method of claim 2, wherein the effector molecule is a chemotherapeutic agent.

5. The method of claim 2, wherein the effector molecule comprises a toxic moiety.

6. The method of claim 5, wherein the toxic moiety is selected from the group consisting of ricin A, abrin, diphtheria toxin or a subunit thereof, *Pseudomonas* exotoxin or a portion thereof, and botulinum toxins A through F.

7. The method of claim 6, wherein the *Pseudomonas* exotoxin is selected from the group consisting of PE35, PE37, PE38, and PE40.

8. The method of claim 1, wherein inhibiting the growth of the basal breast cancer cell comprises reducing metastasis of the basal breast cancer cell in the subject.

9. The method of claim 1, wherein the subject has undergone surgical removal of a triple negative basal breast carcinoma primary tumor; and wherein inhibiting the growth of the basal breast cancer cell comprises preventing tumor recurrence in vivo.

10. The method of claim 1, further comprising administering to the subject an additional chemotherapeutic agent.

11. The method of claim 10, wherein the additional chemotherapeutic agent is a mitotic inhibitor, an alkylating agent, an anti-metabolite, an intercalating antibiotic, a growth factor inhibitor, a cell cycle inhibitor, an enzyme, a topoisomerase inhibitor, an anti-androgen, or an anti-angiogenesis agent.

12. The method of claim 1, wherein the method comprises selecting a subject with metastatic triple negative basal breast cancer.

\* \* \* \* \*

SEQUENCE LISTING

```
<160> NUMBER OF SEQ ID NOS: 5

<210> SEQ ID NO 1
<211> LENGTH: 327
<212> TYPE: PRT
<213> ORGANISM: Homo sapiens

<400> SEQUENCE: 1

Glu Gln Met Arg Glu Glu Pro Glu Ala Ala Tyr Arg Leu Ile Gln Gly
1               5                   10                  15

Pro Gln Tyr Gly His Leu Leu Val Gly Gly Arg Pro Thr Ser Ala Phe
            20                  25                  30

Ser Gln Phe Gln Ile Asp Gln Gly Glu Val Val Phe Ala Phe Thr Asn
        35                  40                  45

Phe Ser Ser Ser His Asp His Phe Arg Val Leu Ala Leu Ala Arg Gly
    50                  55                  60

Val Asn Ala Ser Ala Val Val Asn Val Thr Val Arg Ala Leu Leu His
65                  70                  75                  80

Val Trp Ala Gly Gly Pro Trp Pro Gln Gly Ala Thr Leu Arg Leu Asp
                85                  90                  95

Pro Thr Val Leu Asp Ala Gly Glu Leu Ala Asn Arg Thr Gly Ser Val
            100                 105                 110

Pro Arg Phe Arg Leu Leu Glu Gly Pro Arg His Gly Arg Val Val Arg
        115                 120                 125

Val Pro Arg Ala Arg Thr Glu Pro Gly Gly Ser Gln Leu Val Glu Gln
    130                 135                 140

Phe Thr Gln Gln Asp Leu Glu Asp Gly Arg Leu Gly Leu Glu Val Gly
145                 150                 155                 160

Arg Pro Glu Gly Arg Ala Pro Gly Pro Ala Gly Asp Ser Leu Thr Leu
                165                 170                 175

Glu Leu Trp Ala Gln Gly Val Pro Pro Ala Val Ala Ser Leu Asp Phe
            180                 185                 190

Ala Thr Glu Pro Tyr Asn Ala Ala Arg Pro Tyr Ser Val Ala Leu Leu
        195                 200                 205

Ser Val Pro Glu Ala Ala Arg Thr Glu Ala Gly Lys Pro Glu Ser Ser
```

Thr Pro Thr Gly Glu Pro Gly Pro Met Ala Ser Ser Pro Glu Pro Ala
225                 230                 235                 240

Val Ala Lys Gly Gly Phe Leu Ser Phe Leu Glu Ala Asn Met Phe Ser
            245                 250                 255

Val Ile Ile Pro Met Cys Leu Val Leu Leu Leu Ala Leu Ile Leu
        260                 265                 270

Pro Leu Leu Phe Tyr Leu Arg Lys Arg Asn Lys Thr Gly Lys His Asp
            275                 280                 285

Val Gln Val Leu Thr Ala Lys Pro Arg Asn Gly Leu Ala Gly Asp Thr
        290                 295                 300

Glu Thr Phe Arg Lys Val Glu Pro Gly Gln Ala Ile Pro Leu Thr Ala
305                 310                 315                 320

Val Pro Gly Gln Leu Phe Pro
            325

<210> SEQ ID NO 2
<211> LENGTH: 983
<212> TYPE: DNA
<213> ORGANISM: Homo sapiens

<400> SEQUENCE: 2

```
gggagcagat gagggaggag ccagaggcag cataccgcct catccaggga ccccagtatg    60
ggcatctcct ggtgggcggg cggcccacct cggccttcag ccaattccag atagaccagg   120
gcgaggtggt ctttgccttc accaacttct cctcctctca tgaccacttc agagtcctgg   180
cactggctag ggtgtcaat gcatcagccg tagtgaacgt cactgtgagg gctctgctgc   240
atgtgtgggc aggtgggcca tggccccagg gtgccaccct gcgcctggac cccaccgtcc   300
tagatgctgg cgagctggcc aaccgcacag gcagtgtgcc gcgcttccgc ctcctggagg   360
gaccccggca tggccgcgtg gtccgcgtgc cccgagccag gacggagccc ggggcagcc    420
agctggtgga gcagttcact cagcaggacc ttgaggacgg gaggctgggg ctggaggtgg   480
gcaggccaga ggggagggcc cccggccccg caggtgacag tctcactctg gagctgtggg   540
cacagggcgt cccgcctgct gtggcctccc tggactttgc cactgagcct acaatgctg    600
cccggcccta cagcgtggcc ctgctcagtg tccccgaggc cgcccggacg gaagcaggga   660
agccagagag cagcaccccc acaggcgagc caggccccat ggcatccagc cctgagcccg   720
ctgtggccaa gggaggcttc ctgagcttcc ttgaggccaa catgttcagc gtcatcatcc   780
ccatgtgcct ggtacttctg ctcctggcgc tcatcctgcc cctgctcttc tacctccgaa   840
aacgcaacaa gacgggcaag catgacgtcc aggtcctgac tgccaagccc cgcaacggcc   900
tggctggtga caccgagacc tttcgcaagg tggagccagg ccaggccatc ccgctcacag   960
ctgtgcctgg ccagttattt cca                                           983
```

<210> SEQ ID NO 3
<211> LENGTH: 613
<212> TYPE: PRT
<213> ORGANISM: Pseudomonas aeruginosa

<400> SEQUENCE: 3

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val

```
                35                  40                  45
Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
450                 455                 460
```

```
-continued

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
        530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
                580                 585                 590

Ala Ile Ser Ala Leu Pro Asp Tyr Ala Ser Gln Pro Gly Lys Pro Pro
            595                 600                 605

Arg Glu Asp Leu Lys
        610

<210> SEQ ID NO 4
<211> LENGTH: 4
<212> TYPE: PRT
<213> ORGANISM: Pseudomonas aeruginosa

<400> SEQUENCE: 4

Lys Asp Glu Leu
1

<210> SEQ ID NO 5
<211> LENGTH: 4
<212> TYPE: PRT
<213> ORGANISM: Pseudomonas aeruginosa

<400> SEQUENCE: 5

Arg Glu Asp Leu
1
```